US012702742B2

(12) United States Patent
Pillai

(10) Patent No.: US 12,702,742 B2
(45) Date of Patent: Aug. 11, 2026

(54) METHODS AND DEVICES FOR PERCUTANEOUS IMPLANTATION OF ARTERIO-VENOUS GRAFTS

(71) Applicant: Vascular Access Technologies, Inc., South Jordan, UT (US)

(72) Inventor: Lakshmikumar Pillai, Morgantown, WV (US)

(73) Assignee: Vascular Access Technologies, Inc., South Jordan, UT (US)

(*) Notice: Subject to any disclaimer, the term of this patent is extended or adjusted under 35 U.S.C. 154(b) by 415 days.

(21) Appl. No.: 18/301,931

(22) Filed: Apr. 17, 2023

(65) Prior Publication Data

US 2023/0381395 A1 Nov. 30, 2023

Related U.S. Application Data

(62) Division of application No. 15/855,672, filed on Dec. 27, 2017, now Pat. No. 11,654,224.
(Continued)

(51) Int. Cl.
*A61M 1/36* (2006.01)
*A61B 17/11* (2006.01)
(Continued)

(52) U.S. Cl.
CPC ........... *A61M 1/3655* (2013.01); *A61B 17/11* (2013.01); *A61B 17/3415* (2013.01);
(Continued)

(58) Field of Classification Search
CPC ........... A61M 1/3655; A61M 25/0102; A61M 25/0194; A61M 25/0662;
(Continued)

(56) References Cited

U.S. PATENT DOCUMENTS

| | | | |
|---|---|---|---|
| 4,559,039 | A | 12/1985 | Ash et al. |
| 4,790,825 | A | 12/1988 | Bernstein et al. |

(Continued)

FOREIGN PATENT DOCUMENTS

| | | |
|---|---|---|
| WO | 2004018029 | 3/2004 |
| WO | 2005053547 | 6/2005 |

(Continued)

OTHER PUBLICATIONS

Notice of Allowance dated Jan. 27, 2023 for U.S. Appl. No. 16/557,641.

(Continued)

*Primary Examiner* — Kai H Weng
*Assistant Examiner* — Katherine-Ph Minh Pham
(74) *Attorney, Agent, or Firm* — Dorsey & Whitney LLP

(57) ABSTRACT

Methods, devices, and kits for implanting a vascular graft to perform hemodialysis treatments on patients with renal failure are disclosed. The kits can include access devices comprised of an access catheter having a guidewire lumen and stylet lumen, a guide tube having a curved distal end, a stylet, an actuator handle and a vascular graft. The methods describe techniques for using the described kits and devices for performing vascular procedures, such as percutaneous implantation of the vascular graft.

18 Claims, 23 Drawing Sheets

Related U.S. Application Data

(60) Provisional application No. 62/440,765, filed on Dec. 30, 2016.

(51) Int. Cl.

| | |
|---|---|
| ***A61B 17/34*** | (2006.01) |
| ***A61F 2/06*** | (2013.01) |
| ***A61F 2/07*** | (2013.01) |
| ***A61F 2/95*** | (2013.01) |
| ***A61F 2/966*** | (2013.01) |
| ***A61M 25/00*** | (2006.01) |
| ***A61M 25/01*** | (2006.01) |
| ***A61M 25/06*** | (2006.01) |
| ***A61M 25/09*** | (2006.01) |

(52) U.S. Cl.
CPC ................ *A61F 2/064* (2013.01); *A61F 2/07* (2013.01); *A61F 2/95* (2013.01); *A61M 25/0102* (2013.01); *A61M 25/0194* (2013.01); *A61M 25/0662* (2013.01); *A61M 25/09041* (2013.01); *A61B 2017/1107* (2013.01); *A61B 2017/1135* (2013.01); *A61F 2002/072* (2013.01); *A61F 2/966* (2013.01); *A61M 2025/0095* (2013.01); *A61M 25/0108* (2013.01); *A61M 2025/0197* (2013.01); *A61M 2205/0266* (2013.01)

(58) Field of Classification Search
CPC ........ A61M 25/09041; A61M 25/0108; A61M 2025/0095; A61M 2025/0197; A61M 2205/0266; A61B 17/11; A61B 17/3415; A61B 2017/1107; A61B 2017/1135; A61F 2/064; A61F 2/07; A61F 2/95; A61F 2/966; A61F 2002/072
See application file for complete search history.

(56) References Cited

U.S. PATENT DOCUMENTS

| | | | | |
|---|---|---|---|---|
| 4,966,163 | A | 10/1990 | Kraus et al. | |
| 5,040,540 | A | 8/1991 | Sackner | |
| 5,295,493 | A | 3/1994 | Radisch, Jr. | |
| 5,389,090 | A | 2/1995 | Fischell et al. | |
| 5,421,348 | A | 6/1995 | Larnard | |
| 5,492,530 | A | 2/1996 | Fischell et al. | |
| 5,591,195 | A | 1/1997 | Taheri et al. | |
| 5,685,820 | A | 11/1997 | Riek et al. | |
| 5,733,248 | A | 3/1998 | Adams et al. | |
| 6,047,700 | A | 4/2000 | Eggers et al. | |
| 6,068,638 | A | 5/2000 | Makower | |
| 6,102,926 | A | 8/2000 | Tartaglia et al. | |
| 6,190,353 | B1 | 2/2001 | Makower et al. | |
| 6,217,527 | B1 | 4/2001 | Selmon et al. | |
| 6,379,319 | B1 | 4/2002 | Garibotto et al. | |
| 6,475,226 | B1 | 11/2002 | Belef et al. | |
| 6,485,513 | B1 * | 11/2002 | Fan ........................ | A61F 2/064 623/1.36 |
| 6,508,777 | B1 | 1/2003 | Macoviak et al. | |
| 6,554,792 | B2 | 4/2003 | Hughes | |
| 6,554,794 | B1 | 4/2003 | Mueller et al. | |
| 6,623,480 | B1 | 9/2003 | Kuo et al. | |
| 6,709,444 | B1 | 3/2004 | Makower | |
| 6,726,677 | B1 | 4/2004 | Flaherty et al. | |
| 6,929,633 | B2 | 8/2005 | Evans et al. | |
| 6,955,657 | B1 | 10/2005 | Webler | |
| 7,008,979 | B2 | 3/2006 | Schottman et al. | |
| 7,344,567 | B2 | 3/2008 | Slemker | |
| 7,374,567 | B2 | 5/2008 | Heuser | |
| 7,648,517 | B2 | 1/2010 | Makower et al. | |
| 7,688,517 | B2 | 3/2010 | Omura et al. | |
| 8,019,420 | B2 | 9/2011 | Hine et al. | |
| 8,241,311 | B2 | 8/2012 | Ward et al. | |
| 8,374,680 | B2 | 2/2013 | Thompson | |
| 8,409,236 | B2 | 4/2013 | Pillai | |
| 8,568,435 | B2 | 10/2013 | Pillai et al. | |
| 9,220,874 | B2 | 12/2015 | Pillai et al. | |
| 9,282,967 | B2 * | 3/2016 | Paris ................. | A61B 17/0644 |
| 9,511,214 | B2 | 12/2016 | Pillai | |
| 9,623,217 | B2 | 4/2017 | Pillai | |
| 11,654,266 | B2 | 5/2023 | Pillai | |
| 2001/0010006 | A1 | 7/2001 | Bachinski et al. | |
| 2001/0012924 | A1 | 8/2001 | Milo et al. | |
| 2001/0023346 | A1 | 9/2001 | Loeb | |
| 2001/0034547 | A1 | 10/2001 | Hall et al. | |
| 2002/0004666 | A1 | 1/2002 | Schwager et al. | |
| 2002/0029060 | A1 | 3/2002 | Hogendijk et al. | |
| 2002/0120250 | A1 | 8/2002 | Altman | |
| 2002/0122877 | A1 | 9/2002 | Harish et al. | |
| 2002/0133168 | A1 | 9/2002 | Smedley et al. | |
| 2002/0169377 | A1 | 11/2002 | Khairkhahan et al. | |
| 2003/0040771 | A1 | 2/2003 | Hyodoh | |
| 2003/0078519 | A1 | 4/2003 | Salahieh et al. | |
| 2004/0039371 | A1 | 2/2004 | Tockman et al. | |
| 2004/0059280 | A1 | 3/2004 | Makower et al. | |
| 2004/0082850 | A1 | 4/2004 | Bonner et al. | |
| 2004/0097880 | A1 | 5/2004 | Schur | |
| 2004/0116878 | A1 | 6/2004 | Byrd et al. | |
| 2004/0133168 | A1 | 7/2004 | Salcudean et al. | |
| 2004/0181150 | A1 | 9/2004 | Evans et al. | |
| 2004/0181238 | A1 | 9/2004 | Zarbatany et al. | |
| 2005/0101984 | A1 | 5/2005 | Chanduszko et al. | |
| 2005/0149094 | A1 | 7/2005 | Kasahara et al. | |
| 2005/0149097 | A1 | 7/2005 | Regnell et al. | |
| 2005/0209579 | A1 | 9/2005 | Yacoubian et al. | |
| 2005/0279370 | A1 | 12/2005 | Aboul-Hosn et al. | |
| 2006/0009737 | A1 | 1/2006 | Whiting et al. | |
| 2006/0135962 | A1 | 6/2006 | Kick et al. | |
| 2006/0173440 | A1 | 8/2006 | Lamson | |
| 2006/0189929 | A1 | 8/2006 | Lary et al. | |
| 2006/0247750 | A1 | 11/2006 | Seifert et al. | |
| 2007/0021767 | A1 | 1/2007 | Breznock | |
| 2007/0203515 | A1 | 8/2007 | Heuser et al. | |
| 2008/0082136 | A1 | 4/2008 | Gaudini | |
| 2008/0125748 | A1 | 5/2008 | Patel | |
| 2008/0154172 | A1 | 6/2008 | Mauch | |
| 2008/0171944 | A1 | 7/2008 | Brenneman et al. | |
| 2008/0215008 | A1 | 9/2008 | Nance et al. | |
| 2008/0228171 | A1 | 9/2008 | Kugler et al. | |
| 2008/0249565 | A1 | 10/2008 | Michler et al. | |
| 2009/0024072 | A1 | 1/2009 | Criado et al. | |
| 2009/0112050 | A1 | 4/2009 | Farnan et al. | |
| 2009/0240122 | A1 | 9/2009 | Avitsian | |
| 2010/0185216 | A1 | 7/2010 | Garrison et al. | |
| 2010/0249491 | A1 | 9/2010 | Farnan et al. | |
| 2011/0178530 | A1 | 7/2011 | Bly | |
| 2011/0190871 | A1 | 8/2011 | Trollsas et al. | |
| 2011/0295206 | A1 | 12/2011 | Gurley | |
| 2012/0130468 | A1 | 5/2012 | Khosravi et al. | |
| 2012/0136247 | A1 | 5/2012 | Pillai | |
| 2012/0136366 | A1 | 5/2012 | Pillai | |
| 2012/0290075 | A1 | 11/2012 | Mortisen et al. | |
| 2013/0006282 | A1 | 1/2013 | Wilkinson | |
| 2013/0072957 | A1 | 3/2013 | Anderson | |
| 2013/0324901 | A1 * | 12/2013 | Pillai ................... | A61M 1/3653 604/8 |
| 2013/0324967 | A1 * | 12/2013 | Pillai ................. | A61M 25/0082 604/506 |
| 2014/0018837 | A1 | 1/2014 | Zhou et al. | |
| 2014/0025161 | A1 | 1/2014 | Stankus et al. | |
| 2014/0046346 | A1 | 2/2014 | Hentges et al. | |
| 2014/0107642 | A1 * | 4/2014 | Rios ................... | A61B 17/3478 606/41 |
| 2014/0124418 | A1 | 5/2014 | Ishihara | |
| 2014/0142418 | A1 | 5/2014 | Gurley et al. | |
| 2014/0142677 | A1 | 5/2014 | Heuser et al. | |
| 2014/0288634 | A1 | 9/2014 | Shalev | |
| 2014/0296769 | A1 * | 10/2014 | Hyde .................. | A61M 27/002 604/9 |
| 2015/0320357 | A1 | 11/2015 | Kauaguntla et al. | |
| 2016/0120673 | A1 * | 5/2016 | Siegel ....................... | A61F 2/07 623/1.23 |

(56) References Cited

U.S. PATENT DOCUMENTS

| | | | |
|---|---|---|---|
| 2016/0172922 | A1 | 6/2016 | Kamiya |
| 2017/0035591 | A1 | 2/2017 | De Pablo et al. |
| 2017/0056625 | A1 | 3/2017 | Pillai |
| 2017/0296798 | A1 | 10/2017 | Kume et al. |
| 2018/0161551 | A1 | 6/2018 | Pillai |
| 2019/0321600 | A1 | 10/2019 | Pillai |
| 2020/0069919 | A1 | 3/2020 | Pillai |
| 2020/0338320 | A1 | 10/2020 | Pillai |
| 2022/0401704 | A1 | 12/2022 | Pillai |
| 2023/0218869 | A1 | 7/2023 | Pillai |
| 2023/0381463 | A1 | 11/2023 | Pillai |

FOREIGN PATENT DOCUMENTS

| | | |
|---|---|---|
| WO | 2011068540 | 6/2011 |
| WO | 2013119547 | 8/2013 |

OTHER PUBLICATIONS

Notice of Allowance dated Jan. 27, 2023 for U.S. Appl. No. 15/855,672.
Notice of Allowance dated Jan. 28, 2019 for U.S. Appl. No. 14/949,243.
Notice of Allowance dated Feb. 5, 2020 for U.S. Appl. No. 15/835,114.
Notice of Allowance dated Mar. 19, 2019 for U.S. Appl. No. 15/464,055.
Notice of Allowance dated May 1, 2019 for U.S. Appl. No. 15/347,478.
Notice of Allowance dated Oct. 26, 2022 for U.S. Appl. No. 16/847,281.
Office Action dated Feb. 2, 2021 for U.S. Appl. No. 15/855,672.
Office Action dated Jan. 30, 2018 for U.S. Appl. No. 14/949,243.
Office Action dated Feb. 3, 2021 for U.S. Appl. No. 15/834,998.
Office Action dated Apr. 13, 2020 for U.S. Appl. No. 15/834,998.
Office Action dated Apr. 13, 2022 for U.S. Appl. No. 15/855,672.
Office Action dated May 10, 2022 for U.S. Appl. No. 16/847,281.
Office Action dated May 25, 2021 for U.S. Appl. No. 15/834,998.
Office Action dated May 30, 2017 for U.S. Appl. No. 14/949,243.
Office Action dated Jun. 14, 2018 for U.S. Appl. No. 14/949,243.
Office Action dated Jun. 22, 2021 for U.S. Appl. No. 15/855,672.
Office Action dated Aug. 11, 2022 for U.S. Appl. No. 16/557,641.
Office Action dated Aug. 29, 2019 for U.S. Appl. No. 15/835,114.
Office Action dated Sep. 7, 2018 for U.S. Appl. No. 15/347,478.
Office Action dated Sep. 14, 2022 for U.S. Appl. No. 15/855,672.
Office Action dated Sep. 24, 2020 for U.S. Appl. No. 15/834,998.
Office Action dated Sep. 27, 2018 for U.S. Appl. No. 15/464,055.
Office Action dated Oct. 1, 2021 for U.S. Appl. No. 15/855,672.
Office Action dated Oct. 2, 2018 for U.S. Appl. No. 14/949,243.
Office Action dated Oct. 23, 2019 for U.S. Appl. No. 15/834,998.
Faul , et al., Vascular Disease Management, vol. 5 No. 5, 128-133.
Huang , et al., "Evaluation of the Needle Technique for Producing an Arteriovenous Fistula", Journal of Applied Physiology, vol. 77(6), Dec. 1, 1994, 2907-2911.
Khanna , et al., "sharpening of Hollow Silicon Microneedles to Reduce Skin Penetration Force", Mar. 15, 2010, 045011.
Lumend Inc. , "Outback LTD Re-Entry Catheter; Product Resources (http://www.lumend.com/Images/Technology/Products/brochure.pdf)", Jul. 19, 2006.
Mewissen , "Revascularization of Long FP Arterial Occlusions", Endovascular Today, Mar. 1, 2004, 2-4.
O'Callaghan , et al., "Dynamics of Stab Wounds: Force Required for Penetration of Various Cadaveric Himan Tissues", Forensic Sci. Int'l., vol. 104, Oct. 11, 1999, 173-178.
Office Action dated Feb. 22, 2022 for U.S. Appl. No. 15/834,998.
Office Action dated Sep. 30, 2021 for U.S. Appl. No. 16/503,983.
Office Action dated Nov. 6, 2023 for U.S. Appl. No. 17/810,529.
Office Action dated Feb. 12, 2024 for U.S. Appl. No. 17/810,529.
Office Action dated Jun. 17, 2024 for U.S. Appl. No. 18/065,450.
Office Action dated Aug. 20, 2024 for U.S. Appl. No. 18/302,646.
Welch , et al., "Primary Varicose Veins of the Upper Extremity: A Report of Three Cases", Journal of Vascular Surgery, vol. 20 No. 5, Nov. 1994, 839-843.
Office Action dated Feb. 18, 2025 for U.S. Appl. No. 18/302,646.
Notice of Allowance dated Oct. 30, 2025 for U.S. Appl. No. 18/302,646.

* cited by examiner

METHODS AND DEVICES FOR PERCUTANEOUS IMPLANTATION OF ARTERIO-VENOUS GRAFTS

RELATED CASES

This application is a divisional of U.S. application Ser. No. 15/855,672, filed on Dec. 27, 2017 and titled "METHODS AND DEVICES FOR PERCUTANEOUS IMPLANTATION OF ARTERIO-VENOUS GRAFTS," which claims priority to U.S. Provisional Application No. 62/440,765, filed on Dec. 30, 2016 and titled "PERCUTANEOUS IMPLANTATION OF AN ARTERIO-VENOUS GRAFT," both of which are hereby incorporated by reference in their entireties.

TECHNICAL FIELD

The present disclosure relates to devices and methods for vascular access, including the treatment of patients with renal failure. More specifically, in some embodiments, the present disclosure relates to devices and methods that provide vascular access to treat patients with kidney failure, including percutaneous implantation of arterio-venous grafts.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
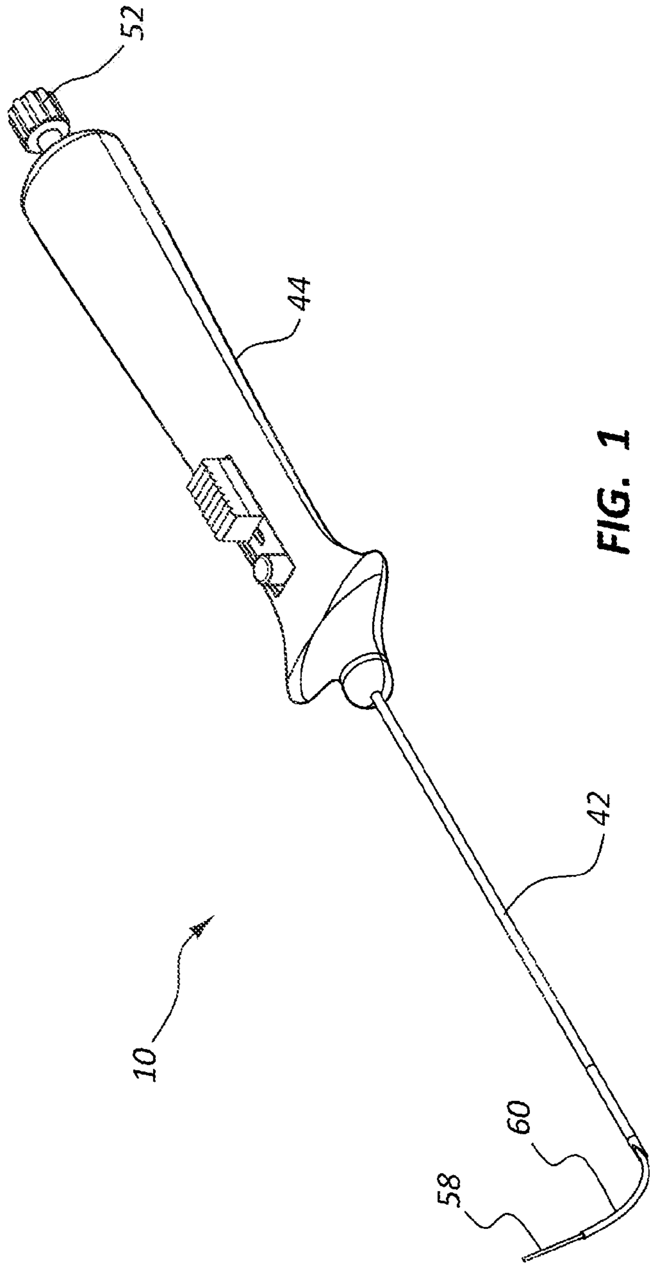
FIG. 1 is a perspective view of an access device.

Vascular access for hemodialysis treatment of kidney failure patients is the lifeline of the patient. Hemodialysis treatment requires access to a patient's vasculature three times a week. Vascular access types include arterio-venous fistula (AVF), arterio-venous graft (AVG) and center venous hemodialysis catheter. The AVF may be beneficial in many instances as it utilizes autogenous vessels. However, the AVF is not suitable for every patient and creation of an AVF requires a surgeon and anesthesia. The AVG is a synthetic graft connecting an artery to a vein. The AVG is normally implanted by a surgeon. However, percutaneous techniques and devices allow for non-surgeons, such as interventionalists, to implant the AVG, reducing the invasiveness of the procedure and potentially reducing procedural costs.

The present disclosure describes access devices and methods for providing a second entry point to a vessel, the second entry point remote from a first entry point. The access devices and methods of the present disclosure may be used to create a vascular access for hemodialysis by percutaneous implantation of a graft. In some embodiments, access devices within the scope of this disclosure include systems comprising: a vascular catheter having first and second lumens, the first lumen being adapted to receive a vascular guidewire; a guide tube disposed in the second lumen, the guide tube having a distal end with a preformed curve; a stylet disposed in the guide tube, the stylet having a sharp distal tip configured to pierce tissue; a guide tube actuator operatively connected to the guide tube or vascular catheter, the guide tube actuator configured to produce relative movement between the guide tube and the vascular catheter; and a stylet actuator operatively connected to the stylet, the stylet actuator having a stylet advancement mechanism. Access devices within the scope of this disclosure may provide a system for accessing an artery and a vein at second sites beyond initial entry sites into the artery and vein and forming a blood flow lumen through subcutaneous space along between the second access sites of the artery and vein.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In the following disclosure, various features are sometimes grouped together in a single embodiment, figure, or description thereof, for the purpose of streamlining the disclosure. Many of these features may be used alone and/or in combination with one another. The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during normal use. The proximal end refers to the opposite end, or the end nearest the practitioner during use. As specifically applied to the access device of the present disclosure, the proximal end of the access device refers to the end nearest the handle and the distal end refers to the opposite end, the end nearest the tip of the catheter. Further, if at one or more points in a procedure a physician changes the orientation of an access device, as used herein, the term "proximal end" always refers to the handle end of the access device (even if the distal end is temporarily closer to the physician).

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

FIGS. 1-5C show various embodiments of devices for percutaneously implanting a graft. For example, the devices disclosed in FIGS. 1-5C may be used in implanting an artereo-venous graft for hemodialysis. The devices shown in FIGS. 1-5C and described in the present disclosure include certain features of those shown in U.S. Pat. No. 9,220,874, the disclosure of which is incorporated herein by reference. As indicated above, FIGS. 1-5C are not necessarily drawn to scale.

Referring to FIG. 1, an access device 10 may comprise a vascular access catheter or first catheter 42, a handle or an actuator 44, a guide tube or cover tube 60, and a stylet 58. The access catheter 42 may be coupled to and extend from the handle 44. The length and diameter of the access catheter 42 may depend on a treatment or anatomy for which the access catheter 42 is intended for use. For example the length of the access catheter 42 may be configured to traverse the distance between a desired entry point into an artery and the location of an occluded portion of the artery. In some embodiments, the length of the access catheter 42 may range from 20 cm to 150 cm, including from 50 cm to 100 cm. The diameter of the access catheter 42 may range from 5 Fr to 9 Fr, including from 6 Fr to 8 Fr.

Figure 2A:
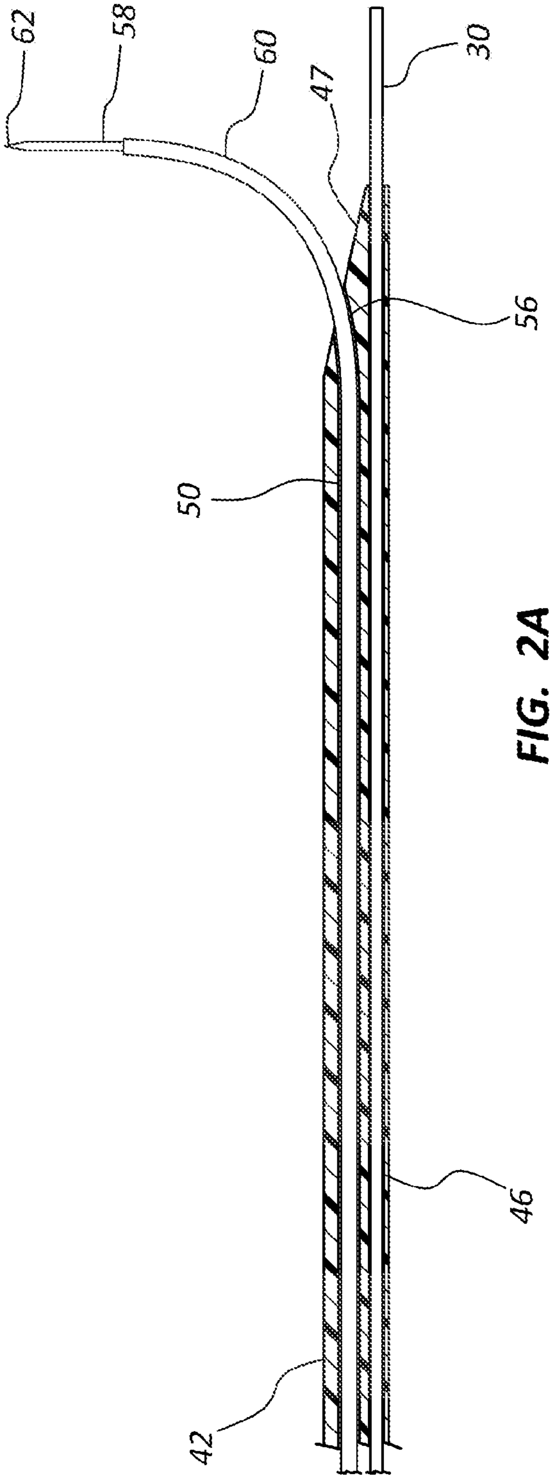
FIG. 2A is a side view of a cross-section of a portion of the access device of FIG. 1 in a first configuration with an extended guide tube and stylet, the access device comprising a ramped surface.
Figure 2B:
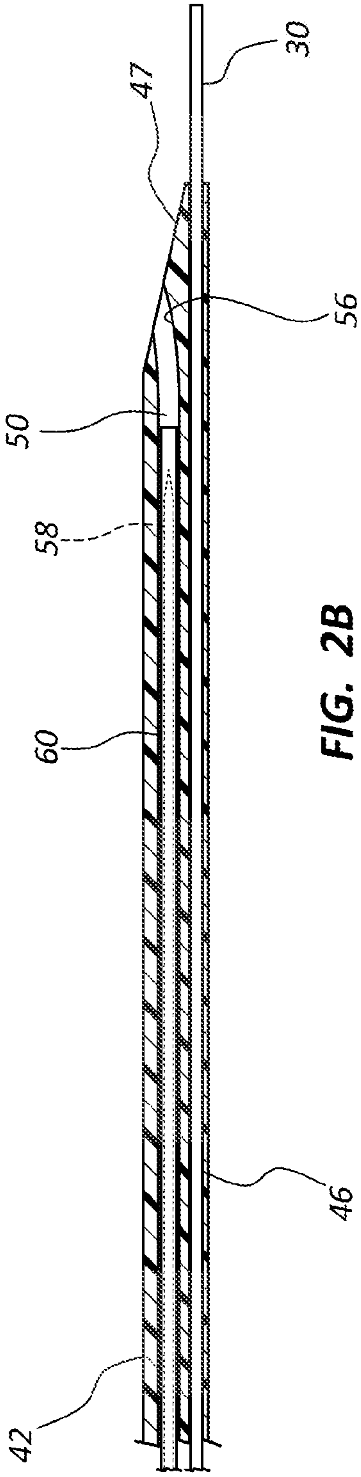
FIG. 2B is a side view of a cross-section of a portion of the access device of FIG. 1 in a second configuration with a retracted guide tube and stylet, the access device comprising a ramped surface.
Figure 3A:
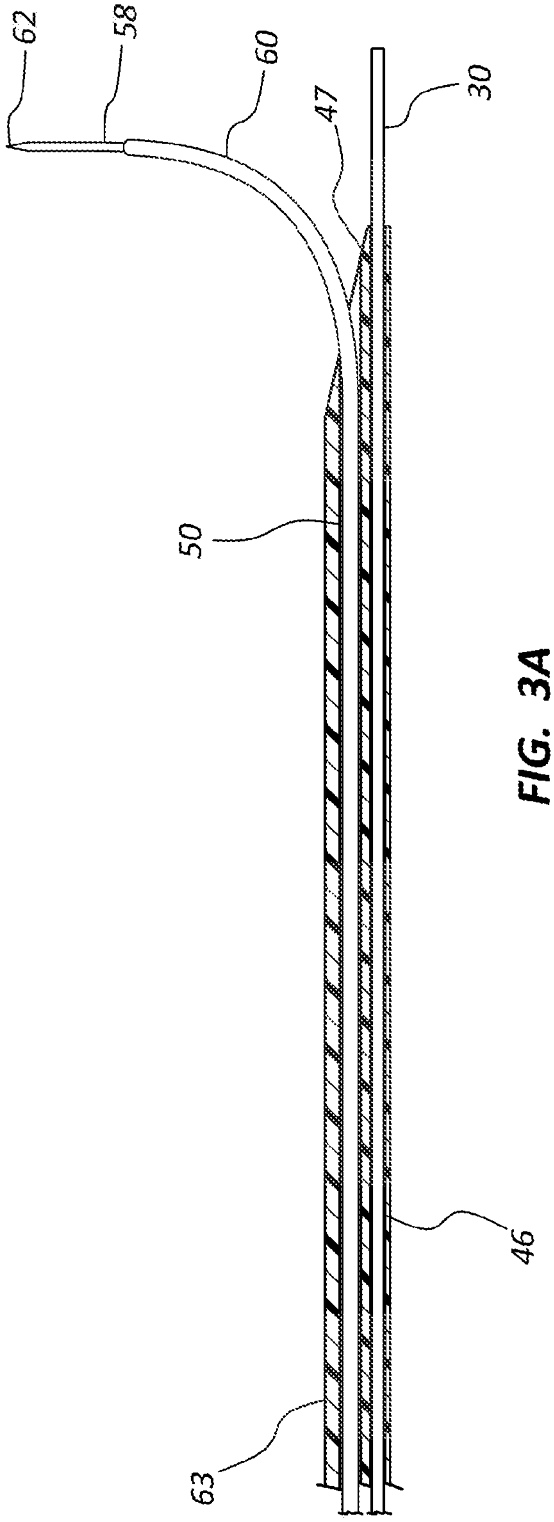
FIG. 3A is a side view of a cross-section of a portion of another embodiment of an access device in a first configuration with an extended guide tube and stylet.
Figure 3B:
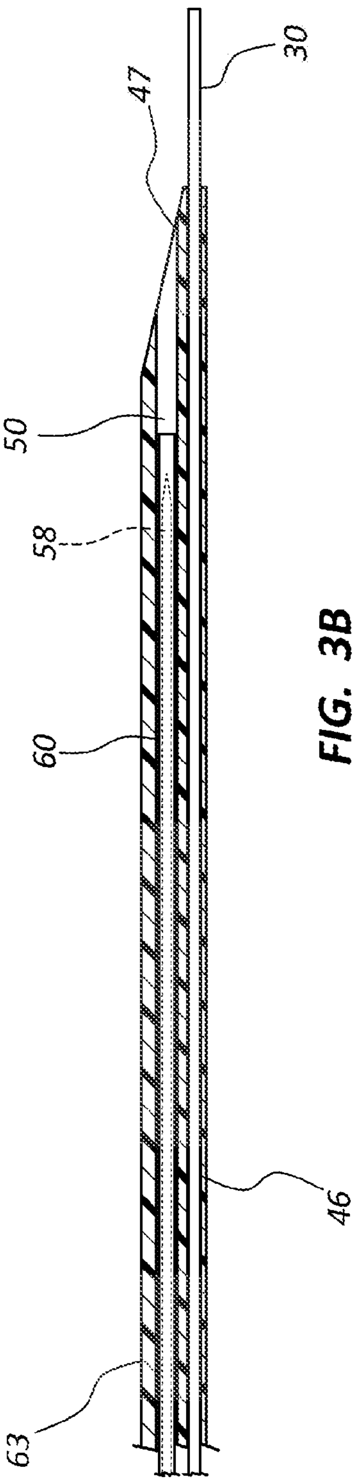
FIG. 3B is a side view of a cross-section of a portion of the access device of FIG. 3A in a second configuration with a retracted guide tube and stylet.

Referring to FIGS. 2A-3B, which illustrate a portion of the access device 10 comprising a distal portion of the access catheter 42 in FIGS. 2A and 2B and an analogous portion of an alternative embodiment of an access catheter 63 in FIGS. 3A and 3B. The access catheters 42 and 63 are shown in cross-section, while the elements disposed within the access catheters 42 and 63 are not in cross-section for clarity. The access catheter 63 of FIGS. 3A and 3B is identical to access the catheter 42 of FIGS. 2A and 2B except that access catheter 63 does not comprise a ramped surface as further detailed below. Accordingly, other elements of the access device 10 of FIG. 1 as shown in FIGS. 3A and 3B (such as a guidewire 30) retain the same numerals as the embodiment of FIGS. 1, 2A and 2B. Disclosure recited in connection with the access catheter 42 of FIGS. 2A and 2B may be analogously applied to the access catheter 63 of FIGS. 3A and 3B.

With continued reference to FIGS. 2A-3B as well as the access device 10 of FIG. 1, the access catheter 42 may comprise a guidewire lumen 46 and a stylet lumen 50. In some embodiments, the guidewire lumen 46 and the stylet lumen 50 may be configured as a single lumen. The guidewire lumen 46 may be sized to receive any suitably sized guidewire, such as 0.014 inch, 0.018 inch, 0.035 inch, etc. The guidewire lumen 46 may be configured as a rapid exchange (RX) guidewire lumen for receiving the guidewire 30. For example, the guidewire lumen 46 may comprise a port adjacent a proximal portion that is configured to receive the guidewire 30. In other embodiments, a wall of the guidewire lumen 46 may be slit adjacent the proximal portion such that the guidewire 30 can be slipped into the guidewire lumen 46 via the slit. Further, in certain embodiments, the guidewire lumen 46 may extend to a proximal end of the access catheter 42 and the guidewire 30 may be advanced through a port (not shown) of the handle 44 into the guidewire lumen 46. Additionally, the guidewire 30 can be introduced into the guidewire lumen 46 using an introducer kit (not shown).

The stylet lumen 50 may extend from the handle 44 to an opening 54 adjacent the distal end of the access catheter 42. In some embodiments, the stylet lumen 50 curves or is ramped at its distal end to form a camming surface 56 as shown in the embodiment of FIGS. 2A and 2B. The camming surface 56 can provide additional structural support and curving guidance to the guide tube 60 when the guide tube 60 is advanced into an extended position. In some embodiments the stylet lumen 50 does not have a curved camming surface. For example, the stylet lumen 50 can be substantially straight adjacent its distal end as illustrated in the embodiment of FIGS. 3A and 3B.

The access catheter 42 comprises a catheter tip 47 at the distal end of the access catheter 42. The catheter tip 47 may be tapered, beveled, or conical, or comprise other shapes or structures. In some embodiments the catheter tip 47 includes a radiopaque marker configured to be visible under fluoroscopy. The radiopaque marker can be embedded in the catheter tip 47. In some embodiments the shape of the radiopaque marker can be selected to facilitate fluoroscopic identification of the location and orientation of the catheter tip 47. Examples of radiopaque marker materials include gold, platinum, platinum-iridium, and other biocompatible radiopaque materials.

The guide tube 60 may be concentrically disposed within the stylet lumen 50 of the access catheter 42. The guide tube 60 may be operatively coupled to the handle 44 and extend from the handle 44 toward the distal end of the access catheter 42. A distal end of the guide tube 60 may be positioned adjacent the catheter tip 47 prior to actuation of the handle 44 as illustrated in the configurations of FIGS. 2B and 3B. In some embodiments, the guide tube 60 may extend beyond the catheter tip 47 following actuation of the handle 44, such as in the configurations shown in FIGS. 2A and 3A. In other embodiments, the guide tube 60 may not extend beyond the catheter tip 47 following actuation of the handle 44, such as embodiments wherein the stylet 58 extends beyond the catheter tip 47 (as further detailed below) but the guide tube 60 remains within the stylet lumen 50 after actuation.

As illustrated in FIGS. 2A and 3A, in some embodiments, the guide tube 60 comprises a preformed curve or bend of substantially 90 degrees at the distal end of the guide tube 60. The range of the angle of the curve or bend may be from 15 degrees to 120 degrees, including 75 degrees to 105 degrees. In some embodiments, the camming surface 56 of the stylet lumen 50 (see the embodiment of FIGS. 2A and 2B) can promote the curvature of the guide tube 60.

The guide tube 60 may be formed of any suitable material such as nickel titanium, shape memory metal, superelastic metal, stainless steel, thermal plastic, etc. The outside diameter of the guide tube 60 may be configured such that the guide tube 60 can be slidably disposed within the stylet lumen 50. The inside diameter of the guide tube 60 may be configured such that the stylet 58 can be slidably disposed within the guide tube 60. For example, the guide tube 60 may be a nitinol hypotube having an outer diameter of 0.025 inch and an inside diameter greater than 0.014 inch such that an 0.014 inch diameter stylet can be disposed with the guide tube 60.

In some embodiments, the stylet 58 may be concentrically disposed within the guide tube 60. The stylet 58 may be operatively coupled to the handle 44 and extend from the handle 44 toward the distal end of the access catheter 42. A distal end of the stylet 58 may be positioned adjacent the distal end of the guide tube 60 prior to actuation of the handle 44 as illustrated in FIGS. 2B and 3B. In some embodiments, the stylet 58 may extend beyond the distal end of the guide tube 60 following actuation of the handle 44 as illustrated in FIGS. 2A and 3A.

The stylet 58 may comprise a sharp distal point 62 adapted to penetrate tissue and other material, such as blood vessel walls and occlusions. The sharp distal point 62 may comprise any suitable design, such as faceted, pencil point, etc. The stylet 58 may be formed of any suitable material such as nickel titanium, shape memory metal, superelastic metal, stainless steel, thermal plastic, etc. The outside diameter of the stylet 58 may be configured such that the stylet 58 can be slidably disposed within the guide tube 60. For example, the stylet 58 may be a nitinol wire having an outer diameter of inch.

Figure 4A:
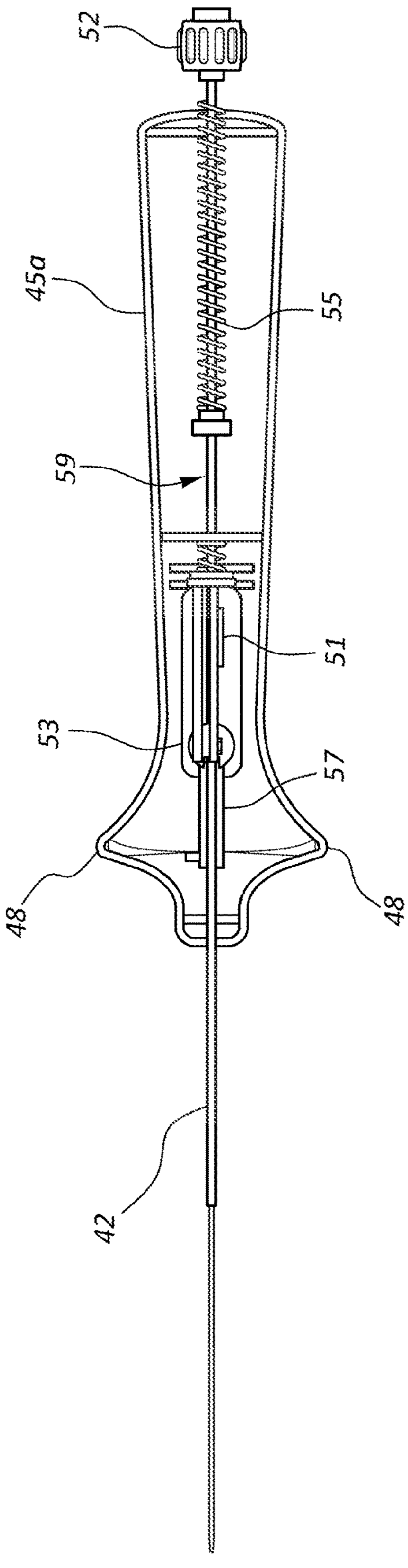
FIG. 4A is a bottom view of the access device of FIG. 1 with a portion of the handle removed to show internal components.
Figure 4B:
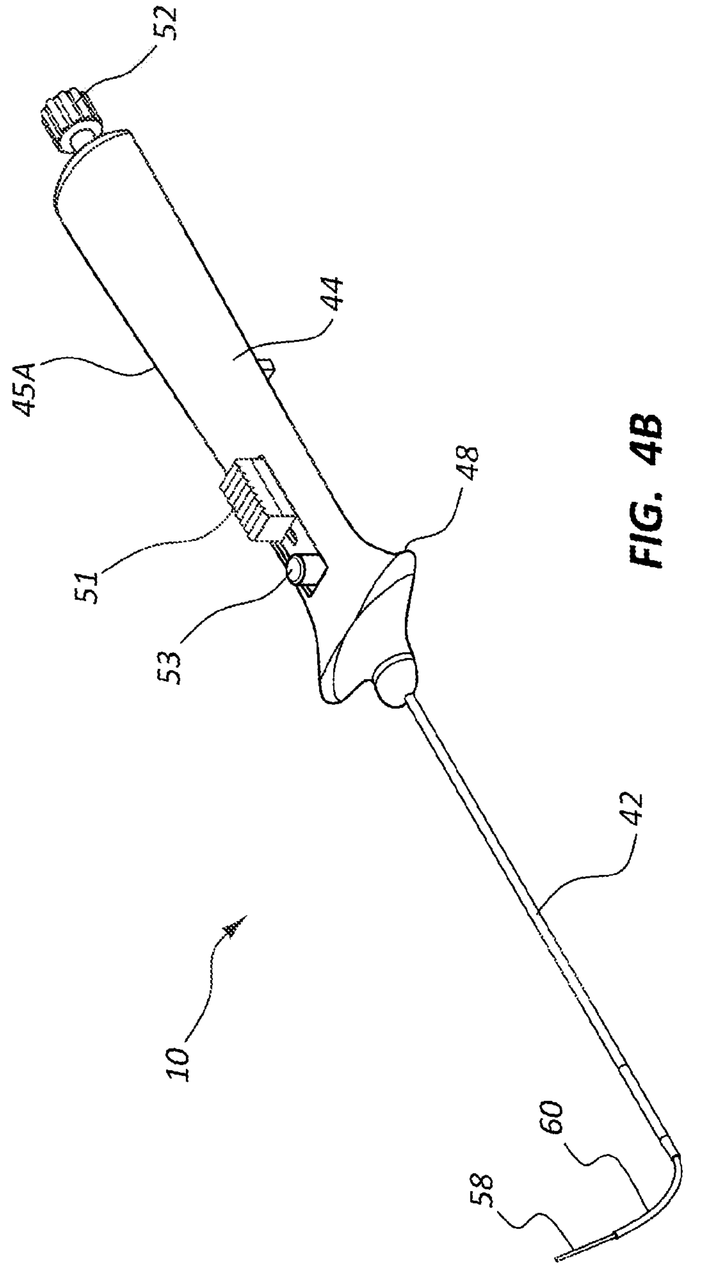
FIG. 4B is a perspective view of a top portion of the handle and other components of the access device of FIG. 1 configured with the guide tube and stylet advanced.
Figure 4C:
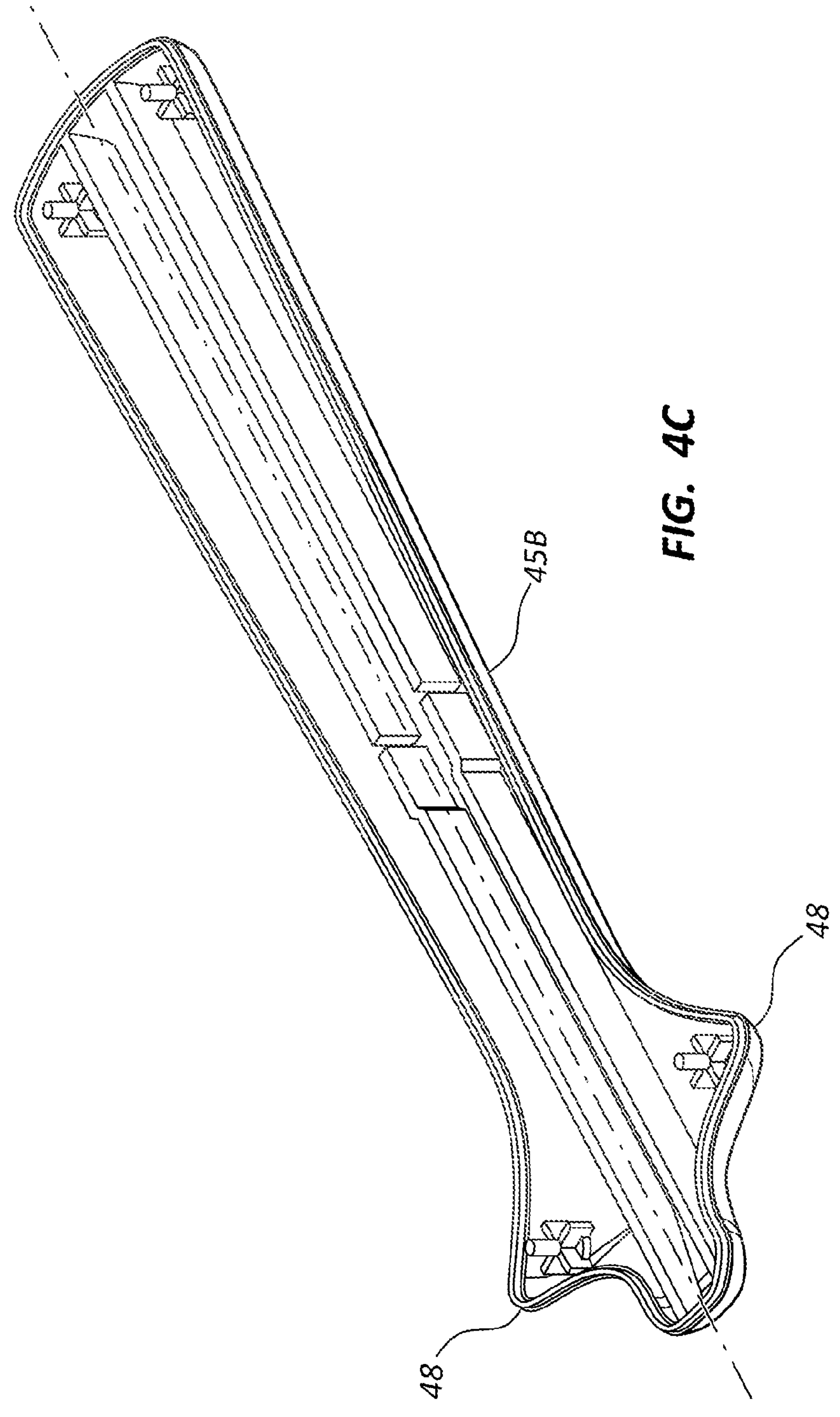
FIG. 4C is a perspective view of a bottom portion of the handle of the access device of FIG. 1.

Referring to FIGS. 4A-4C, in some embodiments the handle 44 can comprise a top portion 45A, a bottom portion 45B, a slide button 51, and a stylet actuator 59. FIG. 4A is a bottom view of the handle 44 with the bottom portion 45B removed to show internal components and the inside of the top portion 45A. FIG. 4B illustrates top view of the handle 44 configured with the guide tube 60 and stylet 58 advanced. FIG. 4C illustrates the bottom portion 45B of the handle 44.

The top portion 45A and bottom portion 45B can engage to form the handle 44. The handle 44 may comprise wings 48 on opposing sides of the handle 44. The wings 48 can be used to apply a distal force to the access catheter 42 from the handle 44 and/or to otherwise manipulate the device.

In some embodiments, a proximal end of the access catheter 42 may be operatively coupled to the slide button 51 via a catheter slide 57. In use, the slide button 51 and catheter slide 57 may be displaced proximally causing the access catheter 42 to be displaced proximally such that the distal end of the guide tube 60 extends from the distal end of the access catheter 42 and assumes a curved shape. (As noted above, the guide tube 60 may be shape-set or otherwise biased to form a curved shape and assume that curved shape when unconstrained by the access catheter 42.) In other embodiments, a proximal end of the guide tube 60 may be operatively coupled to the slide button 51. In such embodiments, the slide button 51 may be displaced distally causing the guide tube 60 to be displaced distally such that the distal end of the guide tube 60 extends from the distal end of the access catheter 42 and assumes its curved shape as illustrated in FIG. 4B.

Figures 5A, 5B, 5C:
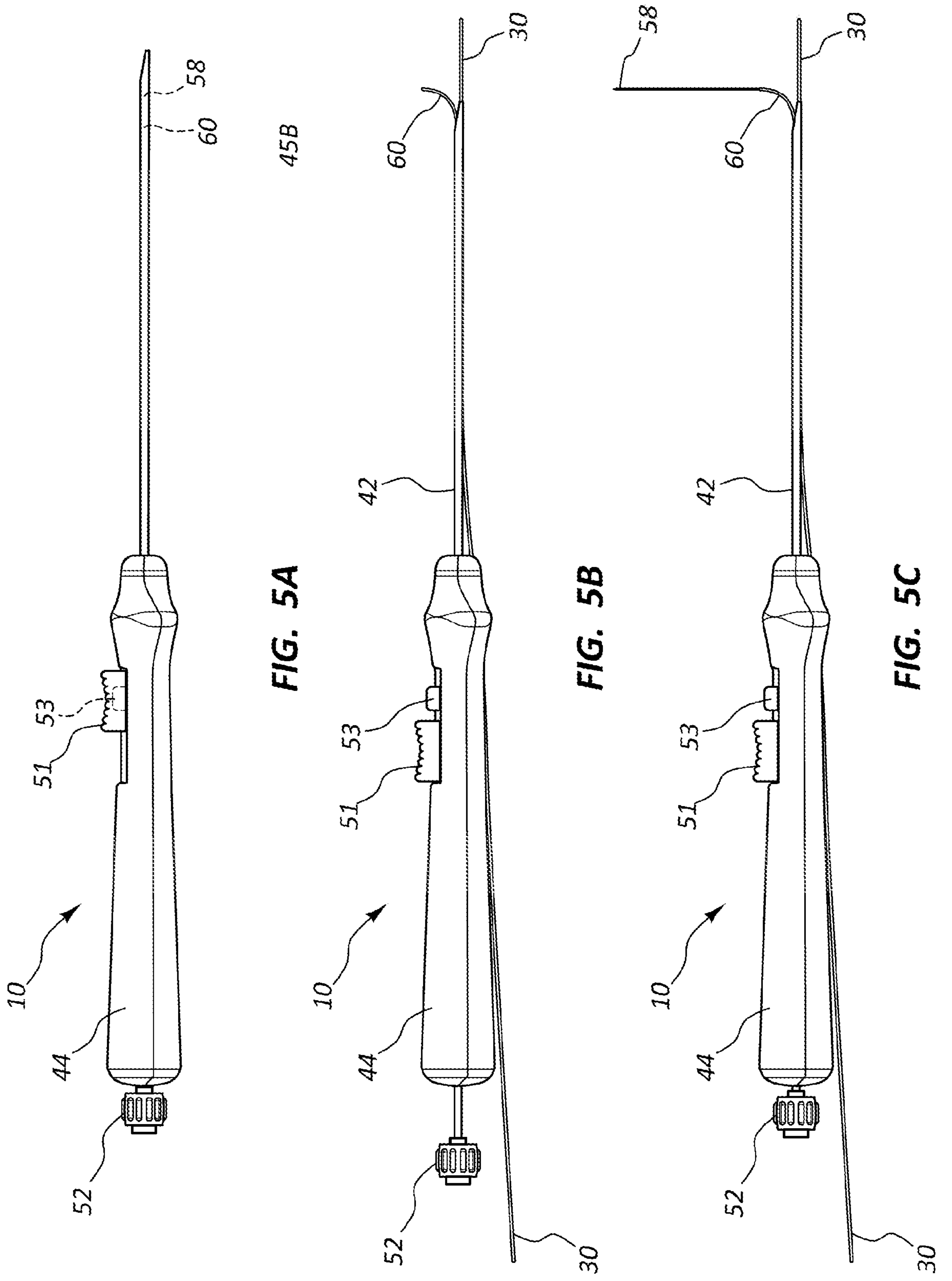
FIG. 5A is a side view of the access device of FIG. 1 prior to advancement of the guide tube.
FIG. 5B is a side view of the access device of FIG. 1 following deployment of the guide tube and loading of a spring loading mechanism.
FIG. 5C is a side view of the access device of FIG. 1 following deployment of the stylet.

Referring to FIGS. 5A-5C as well as the components shown in FIG. 4, in certain embodiments, a proximal portion of the stylet 58 may be operatively coupled to the stylet actuator 59. The stylet actuator 59 may comprise a spring release button 53, a spring loading mechanism 52, and a spring 55 as illustrated in FIG. 4A. The stylet actuator 59 may be configured to displace the stylet 58 such that the distal end of the stylet 58 is displaced through vessel wall tissue and into a vessel lumen. In use, the stylet actuator 59 can be loaded by displacing the spring loading mechanism 52 proximally such that the spring 55 is compressed and the spring loading mechanism 52 is releasably locked in a proximal position. The slide button 51 may cover the spring release button 53 when the access device 10 is in a pre-ready configuration as illustrated in FIG. 5A. The slide button 51 may be displaced proximally, as described previously, such that the spring release button 53 is exposed, such as the configuration shown in FIG. 5B. The spring release button 53 may be positioned either proximal to or distal to the slide button 51. Displacement of the spring release button 53 causes the spring 55 to decompress. The spring loading mechanism 52 is displaced distally as the spring 55 is decompressed. The stylet 58, which is coupled to the spring loading mechanism 52, is displaced distally such that the distal end of the stylet 58 extends from the distal end of the guide tube 60 as illustrated in FIG. 5C.

The access device 10 may be used to perform a variety of vascular procedures, such as transjugular vein carotid artery access, retrograde jugular vein access, bypass graft placement, subintimal angioplasty, hemodialysis graft implantation, etc.

Figure 6A:
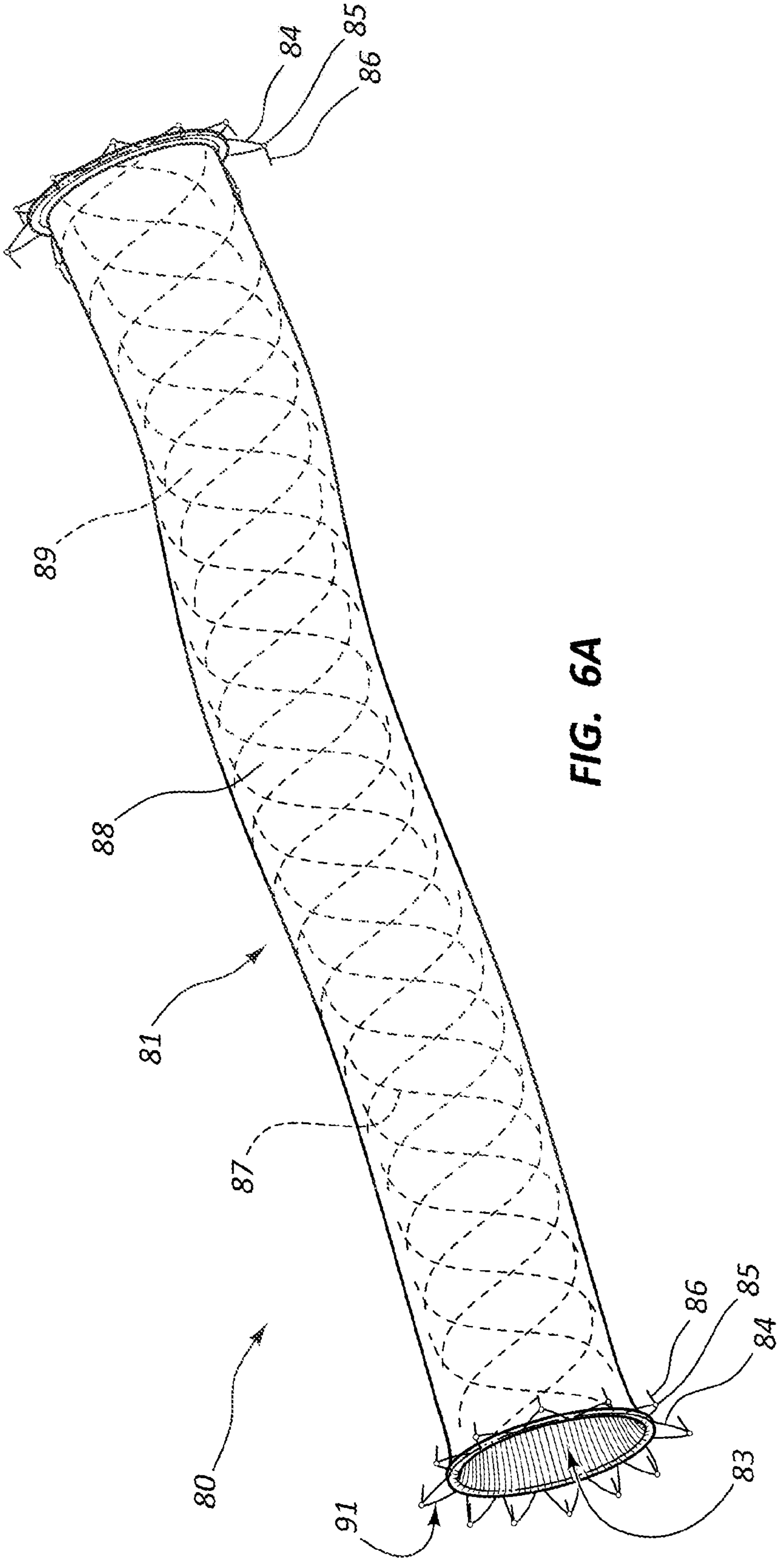
FIG. 6A is a perspective view of an arterio-venousgraft.
Figure 6B:
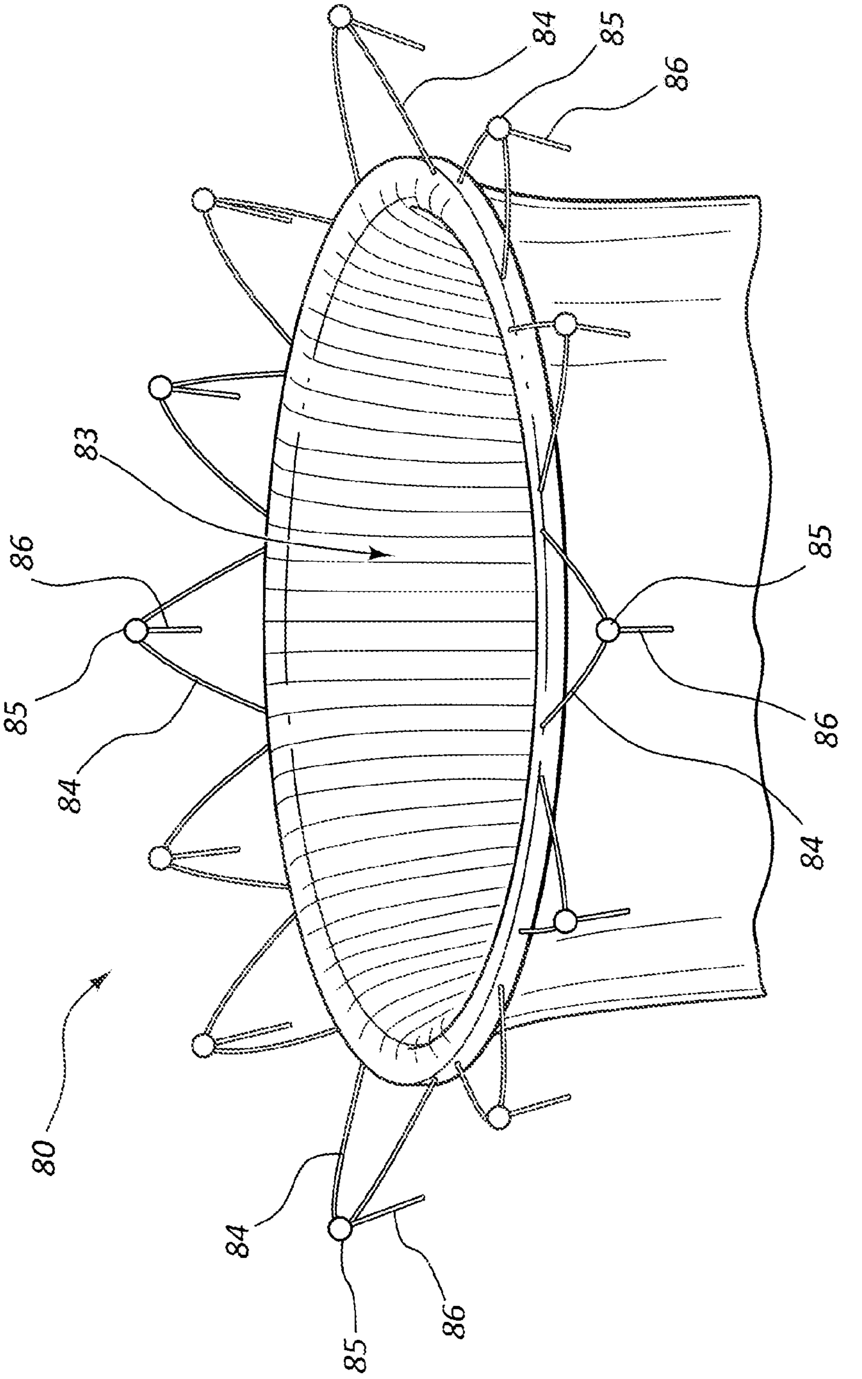
FIG. 6B is a perspective view of an end of the arterio-venous graft of FIG. 6A.
Figure 6C:
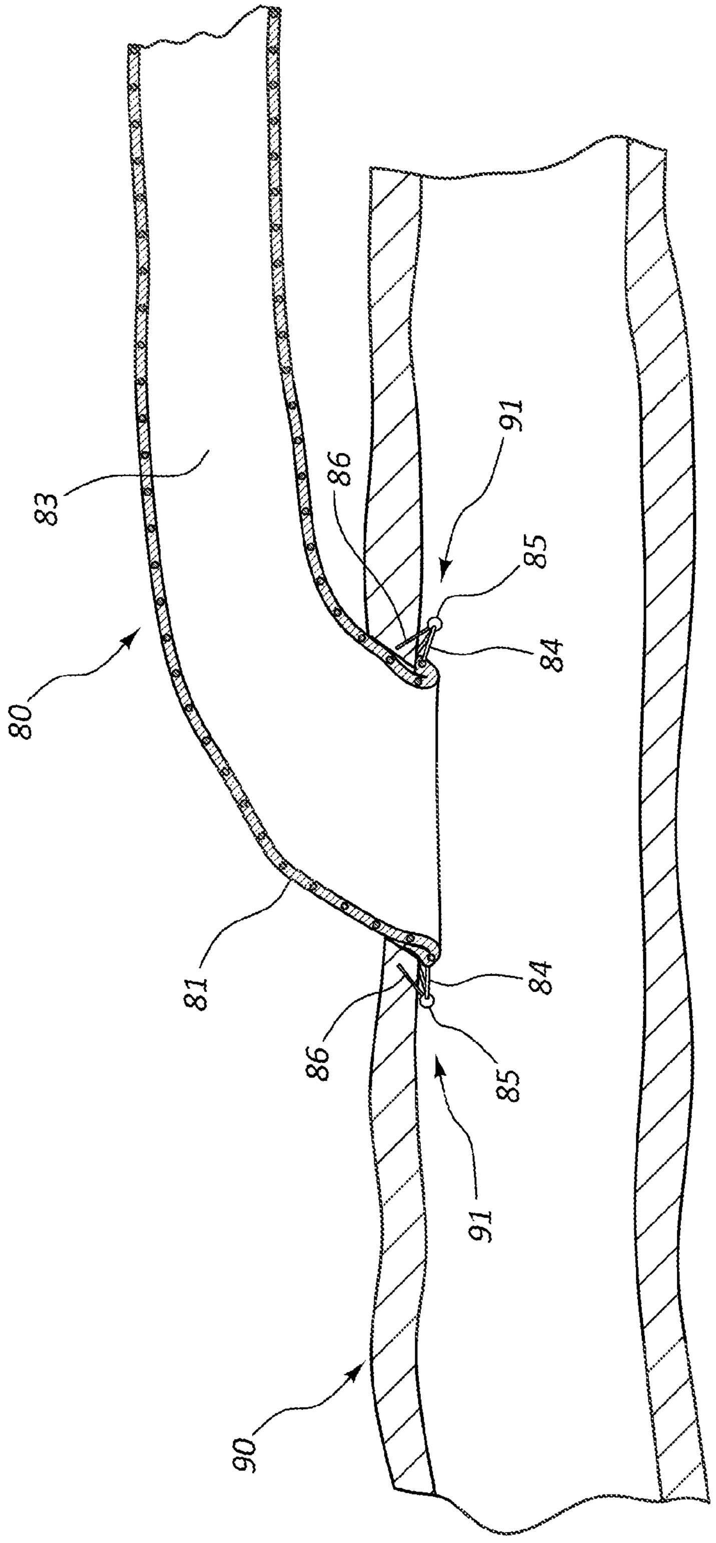
FIG. 6C is a cross-sectional view of a portion of the arterio-venous graft of FIG. 6A coupled to a vessel.

FIGS. 6A-6C illustrate an arterio-venous (AV) graft 80. The AV graft 80 may be configured as a self-expanding, covered stent graft as shown in FIGS. 6A-6C. The access device 10 describe previously may be used to percutaneously implant the AV graft 80 using a method described below. The AV graft 80 may comprise a body 81 and a plurality of anchors 91. The body 81 may be cylindrical in shape and may comprise a frame 87, an internal cover 89, an external cover 88, and a bore 83. The frame 87 may be composed of any suitable memory material, such as nickel titanium alloy (nitinol). The frame 87 may be formed by any suitable technique, such as laser cutting, etching, welding, etc. The structure of the frame 87 may be any suitable structure that allows for radial compression of the frame 87, expansion of the frame 87 upon release of the radial compression, and resistance to radial compression by surrounding tissue.

The covers 88, 89 may be formed of any suitable material such that a lumenal surface is hemocompatable and resistant to thrombus formation. An outer surface may promote tissue ingrowth such that the AV graft 80 is anchored within surrounding subcutaneous tissue when implanted. Examples of suitable materials for the covers 88, 89 are expanded polytetrafluoroethylene (ePTFE), serially deposited PTFE fibers, polyurethane, etc. In some embodiments, the covers 88, 89 may be composed of the same material. In other embodiments, the covers 88, 89 may be composed of different materials to facilitate selected functionality with blood or tissue. In certain, embodiments, the covers 88, 89, may be composed of a combination of materials. In some embodiments, the AV graft may comprise only one cover.

The plurality of the anchors 91 are also shown in FIG. 6B. The anchors 91 may be disposed at either a distal end or proximal end of the body 81. In some embodiments, the anchors 91 are disposed at both the distal and the proximal ends of the body 81. The anchors 91 may comprise at least one strut 84, an apex 85, and a hook 86. The anchors 91 may be coupled to a ring (not shown) that is coupled to an end of the frame 87 and covered by the internal cover 89 and/or the external cover 88. The covers 88, 89 may be coupled to the ring using any suitable technique, such as stitching, gluing, welding, etc. In other embodiments, the anchors 91 may be integral to the frame 87 such that the anchors 91 may be formed as the frame 87 is formed.

The struts 84 may extend radially outward from the end of the body 81. As shown in FIG. 6B, the anchors 91 have two struts 84 configured with a 90 degree angle between the struts 84. In other embodiments, the number of the struts 84 may be 1, 3, 4, or any other suitable number. The struts 84 may merge at the apex 85. The hook 86 may extend along a longitudinal axis of the body 81 toward an opposite end.

FIG. 6C depicts a cross-sectional view of a portion of the covered stent graft 80 in an expanded configuration. The AV graft 80 is shown to be coupled to a vessel 90 forming an anastomosis with the vessel 90. The body 81 of the AV graft 80 is shown to be expanded and extending through an opening in a wall of the vessel 90 such that a seal around the body 81 by the vessel wall is formed to restrict leakage of blood from the vessel. An end of the body 81 is shown to be within the opening such that the bore 83 of the body 81 is in fluid communication with a lumen of the vessel. The hooks 86 of the anchors 91 are shown to be embedded into the vessel wall such that the AV graft 80 is secured to the vessel and axial movement of the AV graft 80 is restricted or prevented.

One exemplary procedure, illustrated in FIGS. 7-13B, is a procedure to percutaneously implant an AV graft to create a vascular access for hemodialysis. The AV graft may be implanted in any suitable location in the patient's body, such as an upper arm, a lower arm, an upper leg, etc. Specific examples include an upper arm loop connecting the brachial artery to an auxiliary vein, a thigh loop graft connecting the femoral artery to the femoral vein, a forearm loop graft, and other locations. Various locations wherein a stent graft may be used percutaneously to connect an artery and a vein are within the scope of this disclosure. FIGS. 7-13B depict the AV graft being implanted in the right upper arm such that the AV graft is coupled to the brachial artery at one end and the axillary vein at the opposite end. The access sites for the access devices used in the procedure are a femoral vein and a femoral artery. Other access sites, such as contralateral brachial artery and basilic vein, are contemplated within the scope of this application. The exemplary procedure may be performed by an interventionalist in a intervention suite. General sedation of the patient and use of a local anesthetic may be administered to the patient for anesthesia.

FIGS. 7-13B show arterial and venous vessels of the patient in cross-section with the elements of the access devices and AV graft implantation elements disposed in various locations during the procedure. The implements are not shown in cross-section for clarity. The cross-sectional plane for FIGS. 7-13B is a plane that includes the longitudinal axis of the vessels.

Figure 7:
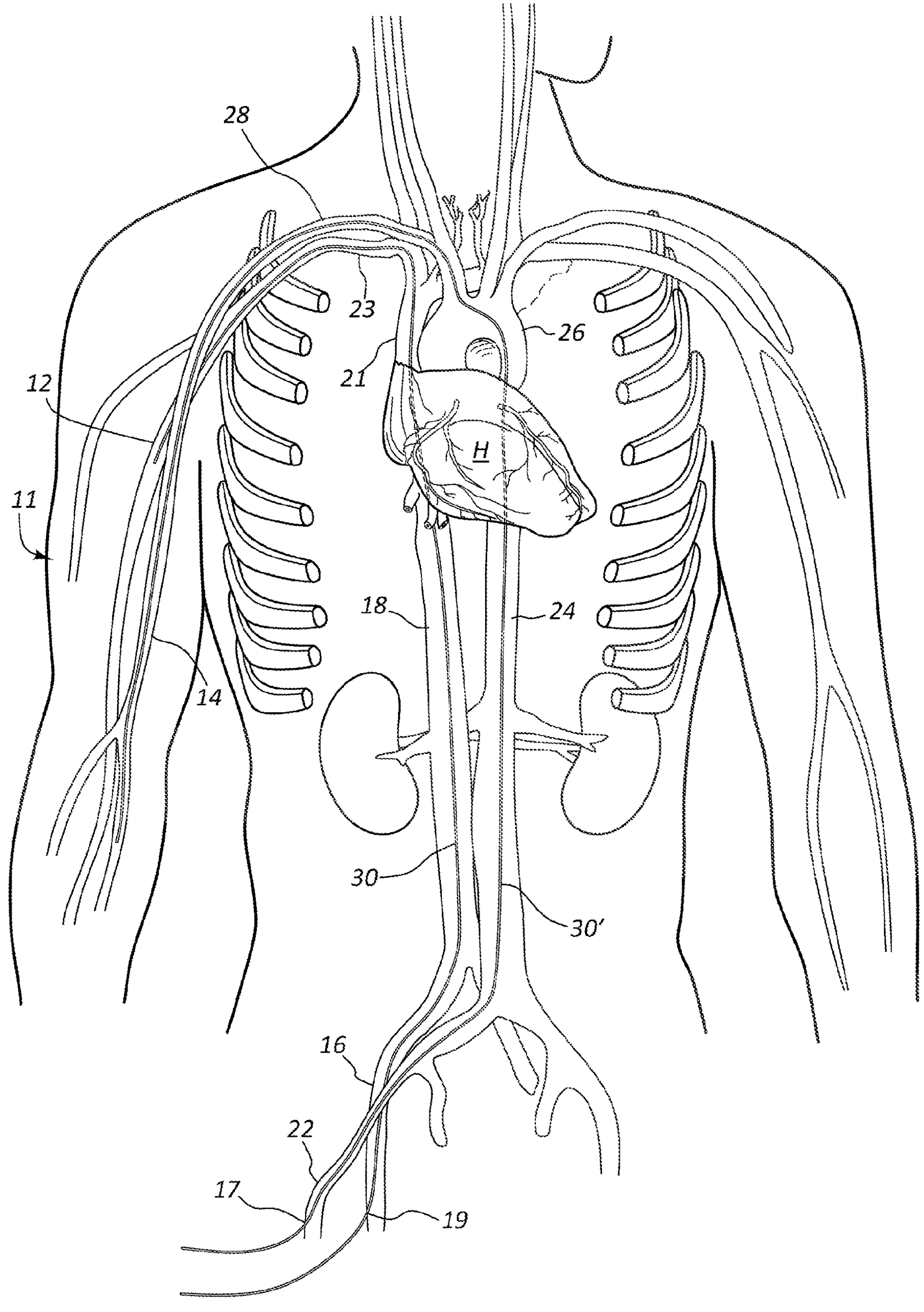
FIG. 7 is a schematic, cross-sectional view of arterial and venous vasculatures of a patient illustrating guidewires within the arterial and venous vasculatures.

As shown in FIG. 7, a first guidewire 30' is inserted into a femoral artery 22 at an arterial access site 17 using an insertion technique such as a Seldinger technique or a modified Seldinger technique with a micropuncture needle and dilator. The access may be performed under an imaging technique such as fluoroscopy or ultrasound. The guidewire 30' is advanced through the arterial vasculature, such as a descending aorta 24, an aortic arch 26, a subclavian artery 28, and a brachial artery 14. A distal end is A distal portion of the guidewire 30' is positioned within a distal portion of the right brachial artery 14 of a right upper arm 11. Advancement of the guidewire 30' may be facilitated by use of fluoroscopy or other suitable imaging technique. Using a similar access technique, a second guidewire 30 is inserted into a femoral vein 16 at a venous access site 19. The guidewire 30' is advanced through the venous vasculature, such as an inferior vena cava 18, a superior vena cava 21, a subclavian vein 23, and an axillary vein 12. A distal portion of the guidewire 30' is positioned in the axillary vein 12 of the right upper arm 11.

Figure 8A:
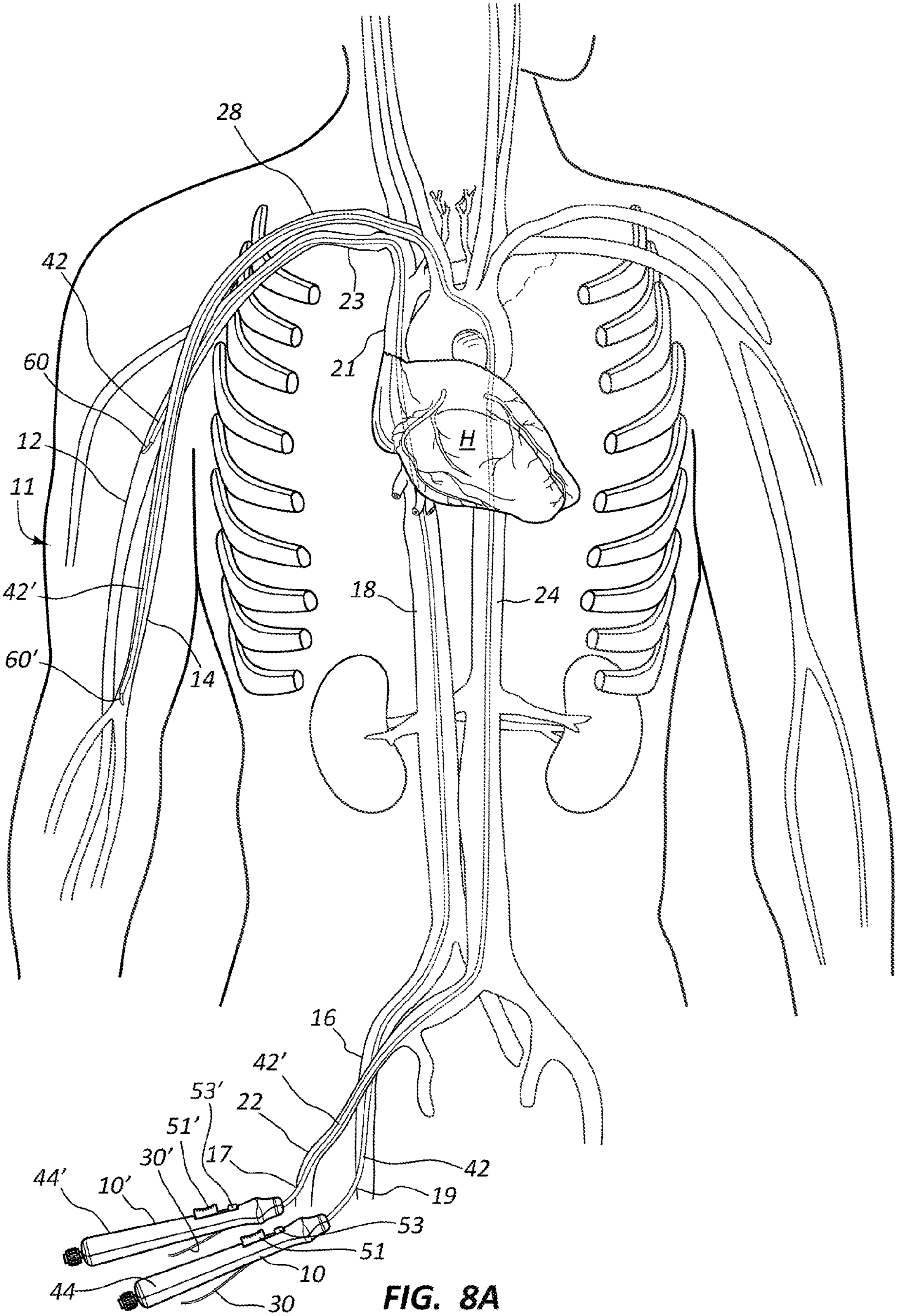
FIG. 8A is a schematic cross-sectional view of arterial and venous vasculatures of the patient illustrating first and second access catheters of the access device of FIG. 1 within the brachial artery and the axillary vein respectively.
Figure 8B:
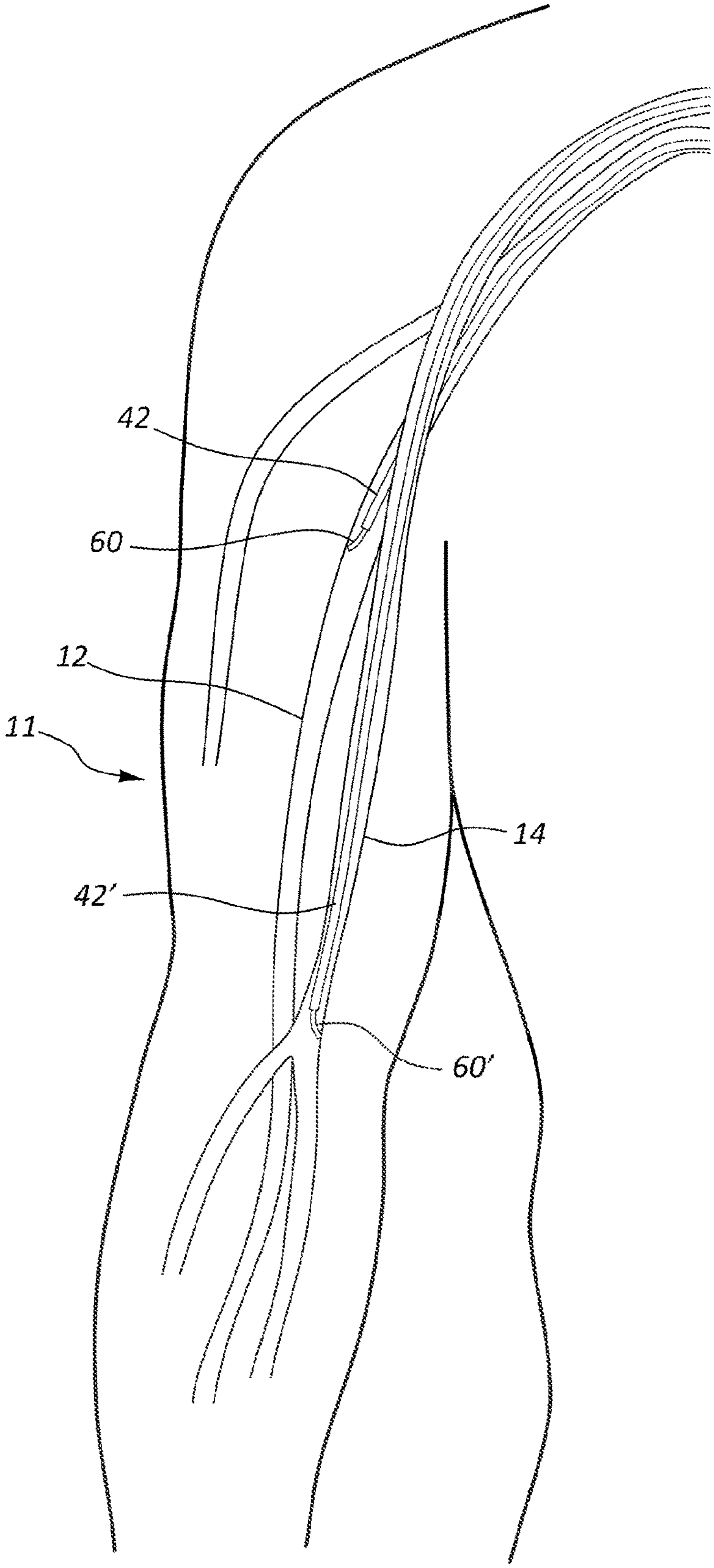
FIG. 8B is a schematic cross-sectional view of the arterial and venous vasculature of the patient's upper right arm illustrating first and second access catheters of the access device of FIG. 1 within the brachial artery and the axillary vein respectively.

FIGS. 8A and 8B illustrate insertion and positioning of the access device 10'. A first access catheter 42' of the access device 10' is threaded over a proximal end of the guidewire 30' and advanced over the guidewire 30' through the arterial vasculature until a distal end of the access catheter 42' is positioned in the brachial artery 14. The access catheter 42' may be advanced over the guidewire 30' and properly positioned using fluoroscopy or any other suitable imaging technique. The distal end of the access catheter 42' is oriented such that a first guide tube 60' is directed toward a wall of the brachial artery 14. Manipulation of the guide tube 60' orientation may be facilitated by rotation of a handle 44' of the access device 10' such that a slider 51' aligns with the desired orientation of the guide tube 60'. The guide tube 60' is extended from the distal end of the access catheter 42' by displacing the slider 51' proximally. The guidewire 30' is removed from the access catheter 42'.

A second access catheter 42 is positioned in the axillary vein 12 using a similar technique as described above. The second access catheter 42 is threaded over a proximal end of a guidewire 30 and advanced over the guidewire 30 through the venous vasculature until a distal end of the second access catheter 42 is positioned within the axillary vein 12. A second guide tube 60 is oriented, as described above, such that the second guide tube 60 is directed toward a wall of the axillary vein 12. The second guide tube 60 is extended from the distal end of the second access catheter 42 by proximal displacement of a slider 51 of handle 44. The guidewire 30 is removed from the second access catheter 42.

Figure 9A:
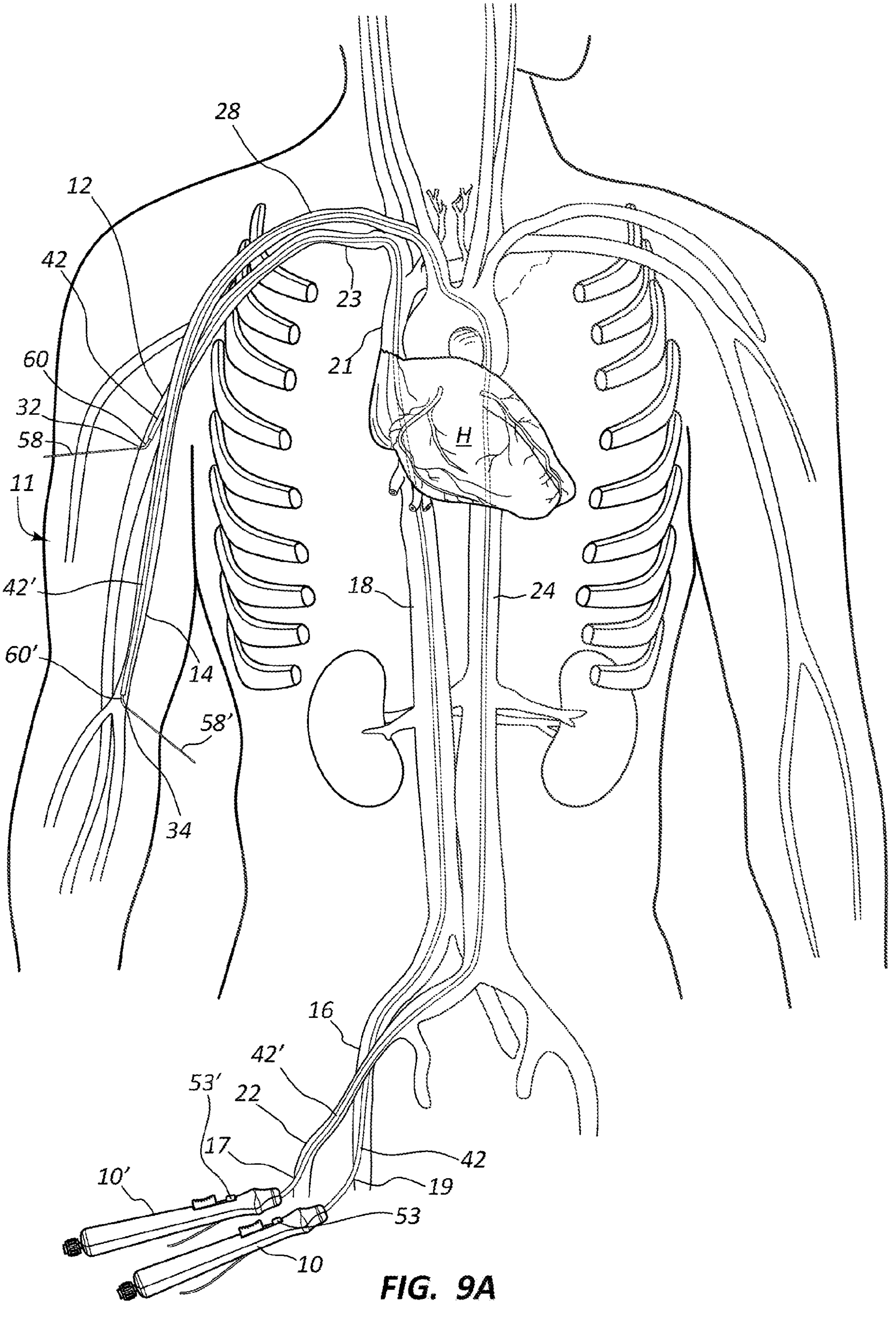
FIG. 9A is a schematic cross-sectional view of arterial and venous vasculatures of the patient illustrating first and second access catheters of the access device of FIG. 1 within the brachial artery and the axillary vein respectively and first and second stylets penetrating a wall of the brachial artery and a wall of the axillary vein respectively.
Figure 9B:
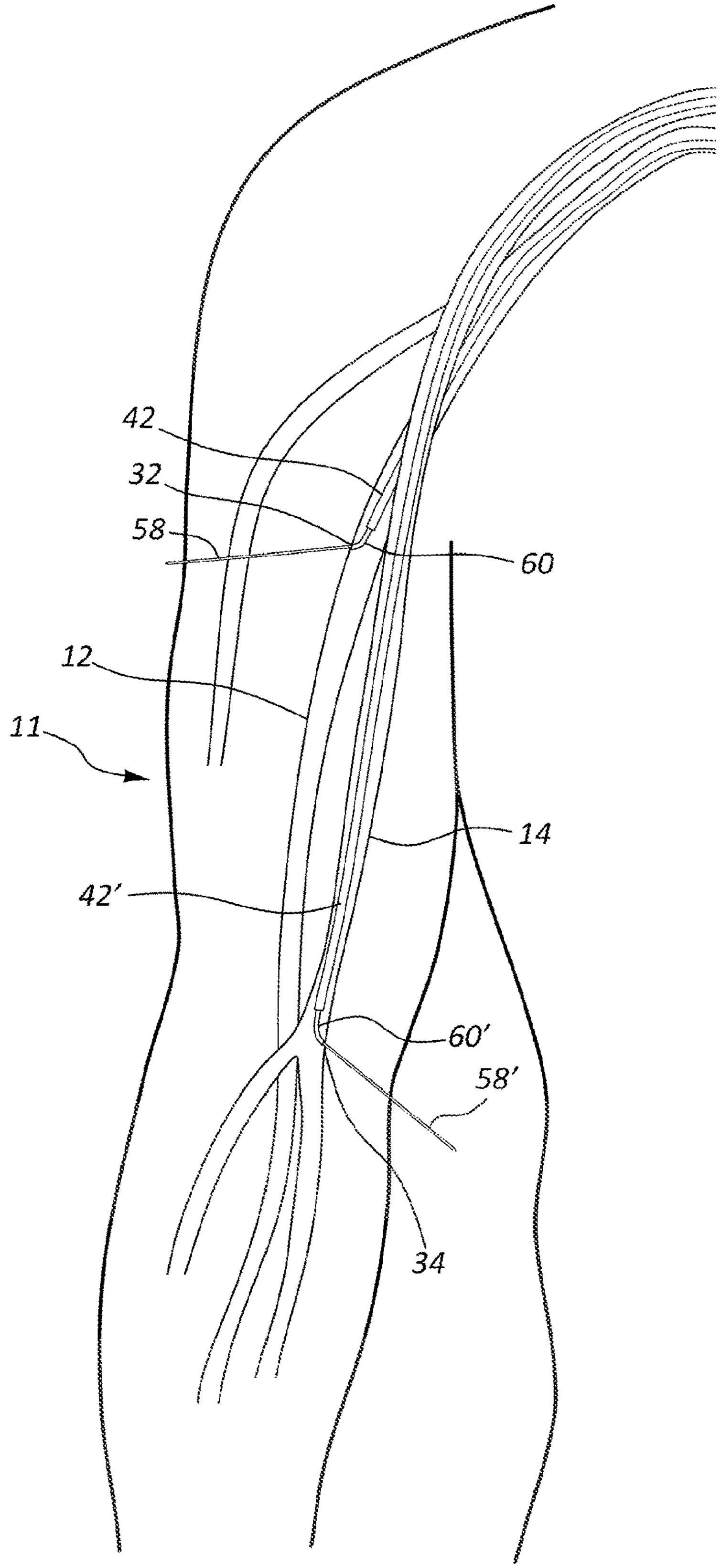
FIG. 9B is a schematic cross-sectional view of the arterial and venous vasculature of the patient's right arm illustrating first and second access catheters of the access device of FIG. 1 within the brachial artery and the axillary vein respectively, and first and second stylets penetrating a wall of the brachial artery and a wall of the axillary vein respectively.

FIGS. 9A and 9B depict deployment of the stylets 58, 58' from the guide tubes 60, 60'. Stylets 58, 58' are deployed by depression of buttons 53, 53' of the access devices 10, 10' respectively. When deployed, the distal end of the stylet 58' extends from guide tube 60' and penetrates a wall of the brachial artery 14 forming an arterial exit site 34. Additionally, the stylet 58' may penetrate and pass through subcutaneous tissue and skin adjacent the brachial artery 14 such that the distal end of the stylet 58' is disposed outside of the right upper arm 11. When deployed, the distal end of the stylet 58 penetrates extends from guide tube 60 and passes through a wall of the axillary vein 12 forming a venous exit site 32. Additionally, the stylet 58 may penetrate and pass through subcutaneous tissue and skin adjacent the axillary vein 12 such that the distal end of the stylet 58 is disposed outside the right upper arm 11.

Figure 10A:
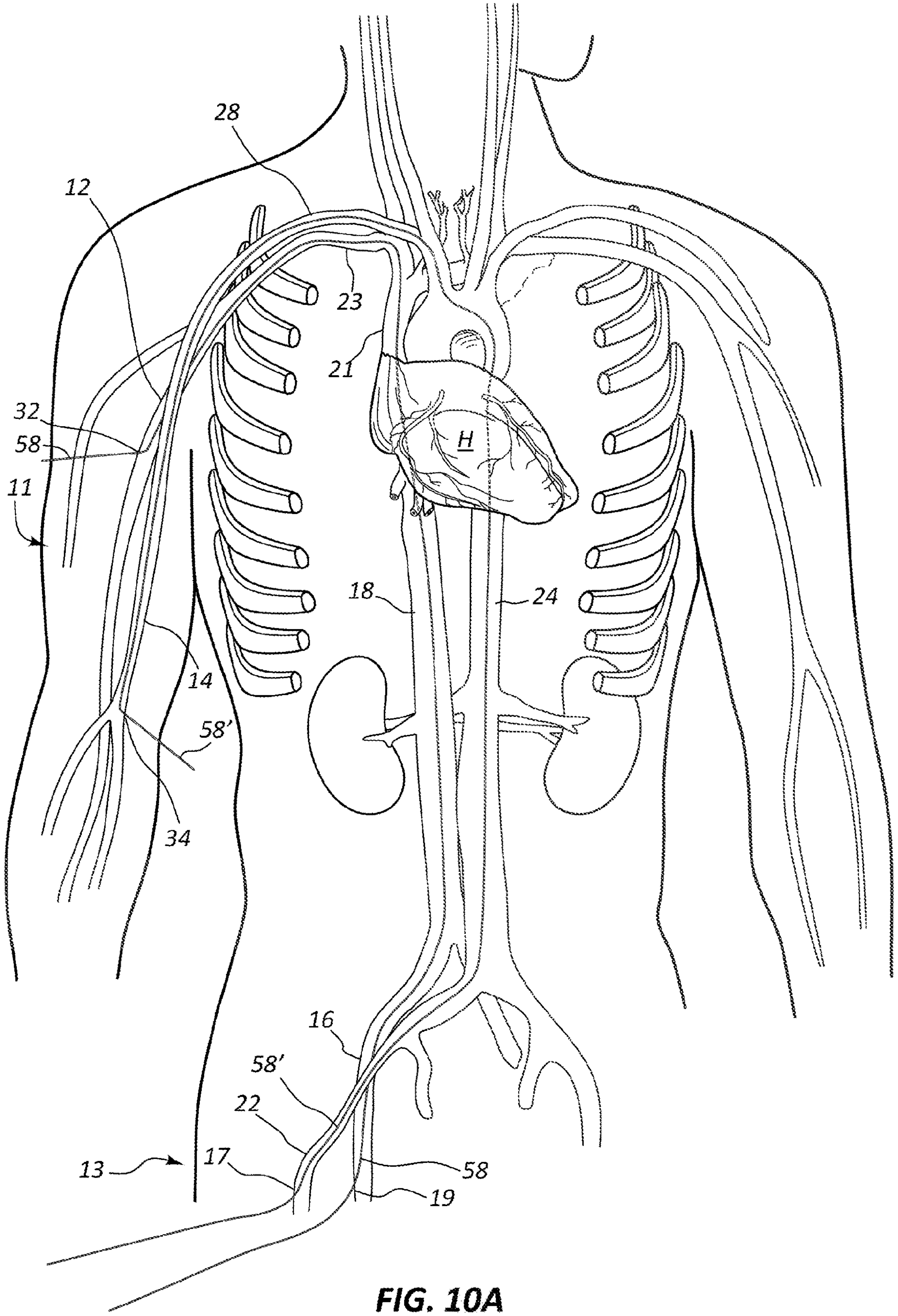
FIG. 10A is a schematic cross-sectional view of arterial and venous vasculatures of the patient illustrating first and second stylets of the access device of FIG. 1 penetrating the wall of the brachial artery and penetrating the wall of the axillary vein, respectively, with first and second access catheters removed
Figure 10B:
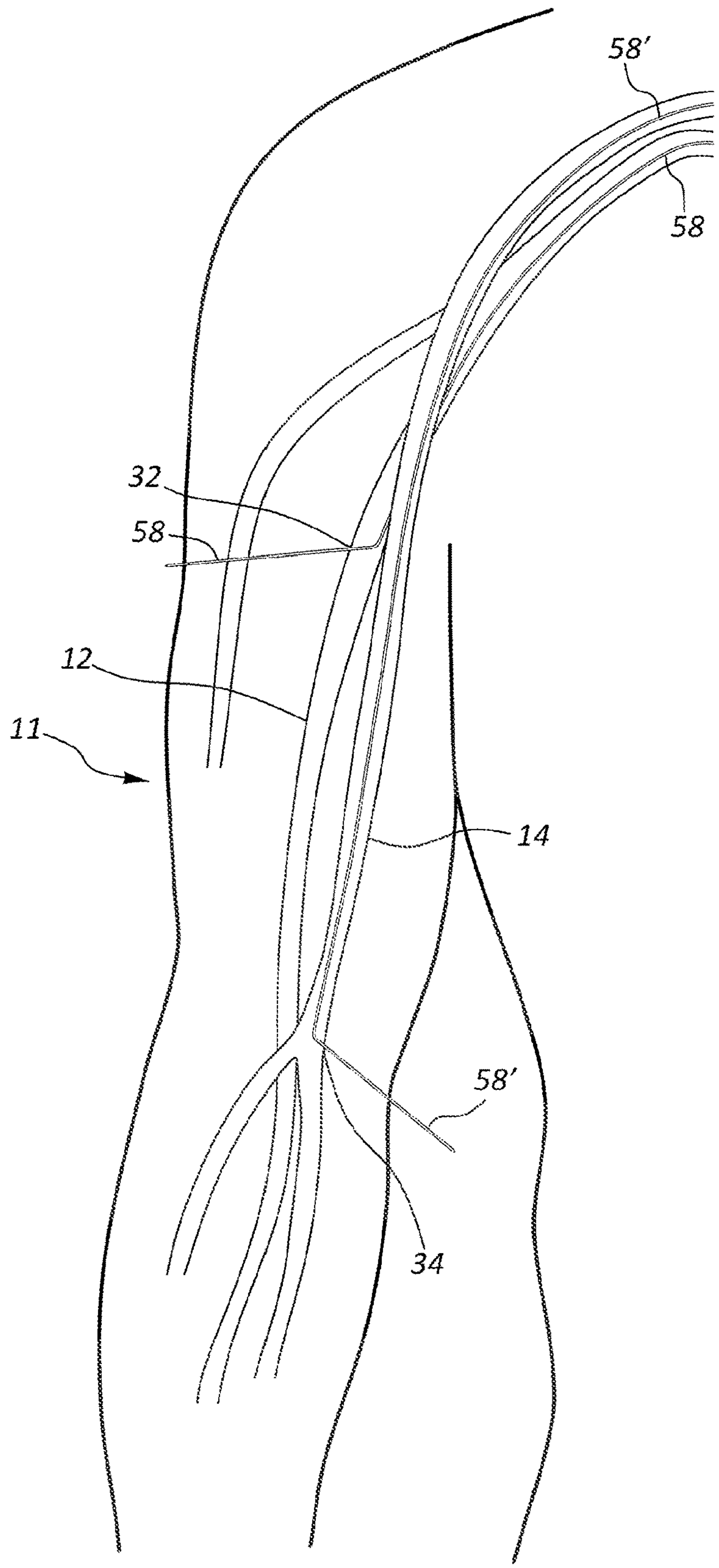
FIG. 10B is a schematic cross-sectional view of the arterial and venous vasculature of the patient's right arm illustrating first and second stylets of the access device of FIG. 1 penetrating the wall of the brachial artery to form an arterial exit site and penetrating the wall of the axillary vein to form a venous exit site, respectively, with first and second access catheters removed.

Referring to FIGS. 10A and 10B, the stylet 58' is depicted with the access catheter 42' removed. The proximal end of the stylet 58' is disposed outside an upper leg 13 of the patient. The stylet 58' passes through skin and subcutaneous tissue adjacent the femoral artery 22 and into the femoral artery 22 through the arterial access site 17. The stylet 58' passes through the arterial vasculature and exits the brachial artery 14 at the arterial exit site 34. The stylet 58' may pass through subcutaneous tissue and skin adjacent the brachial artery 14 such that the distal end of the stylet 58' is disposed outside right upper arm 11.

With continued reference to FIGS. 10A and 10B, the stylet 58 is illustrated with the access catheter 42 removed. The proximal end of the stylet 58 is disposed outside the upper leg 13 of the patient. The stylet 58 passes through skin and subcutaneous tissue adjacent the femoral vein 16 and into the femoral vein 16 through the venous access site 19. The stylet 58 passes through the venous vasculature and exits the axillary vein 12 at the venous exit site 32 and passes through subcutaneous tissue and skin adjacent to the axillary vein 12 such that the distal end of stylet 58 is disposed outside right upper arm 11.

Figure 11A:
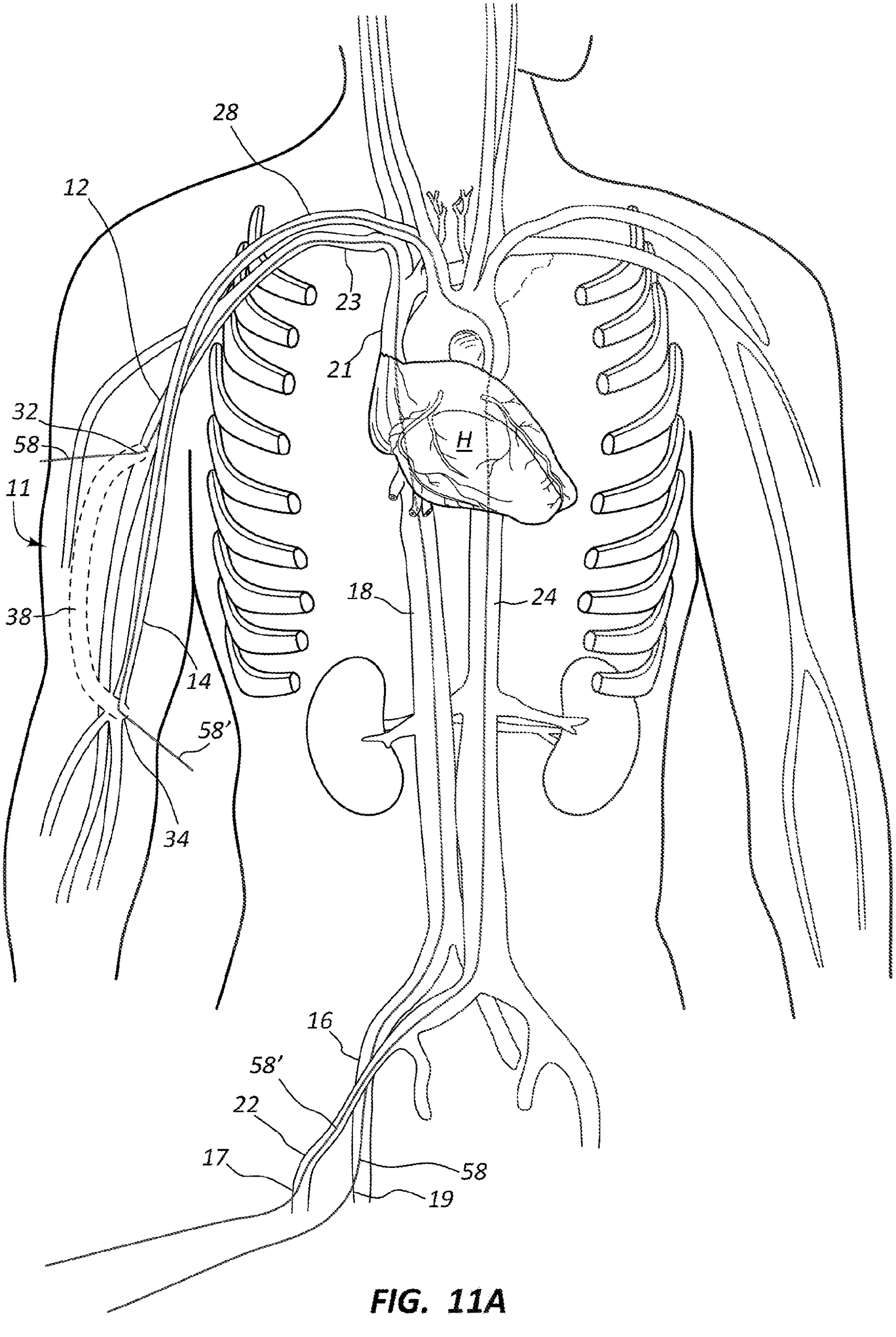
FIG. 11A is a schematic cross-sectional view of arterial and venous vasculatures of the patient illustrating a subcutaneous tunnel between the arterial exit site and the venous exit site.
Figure 11B:
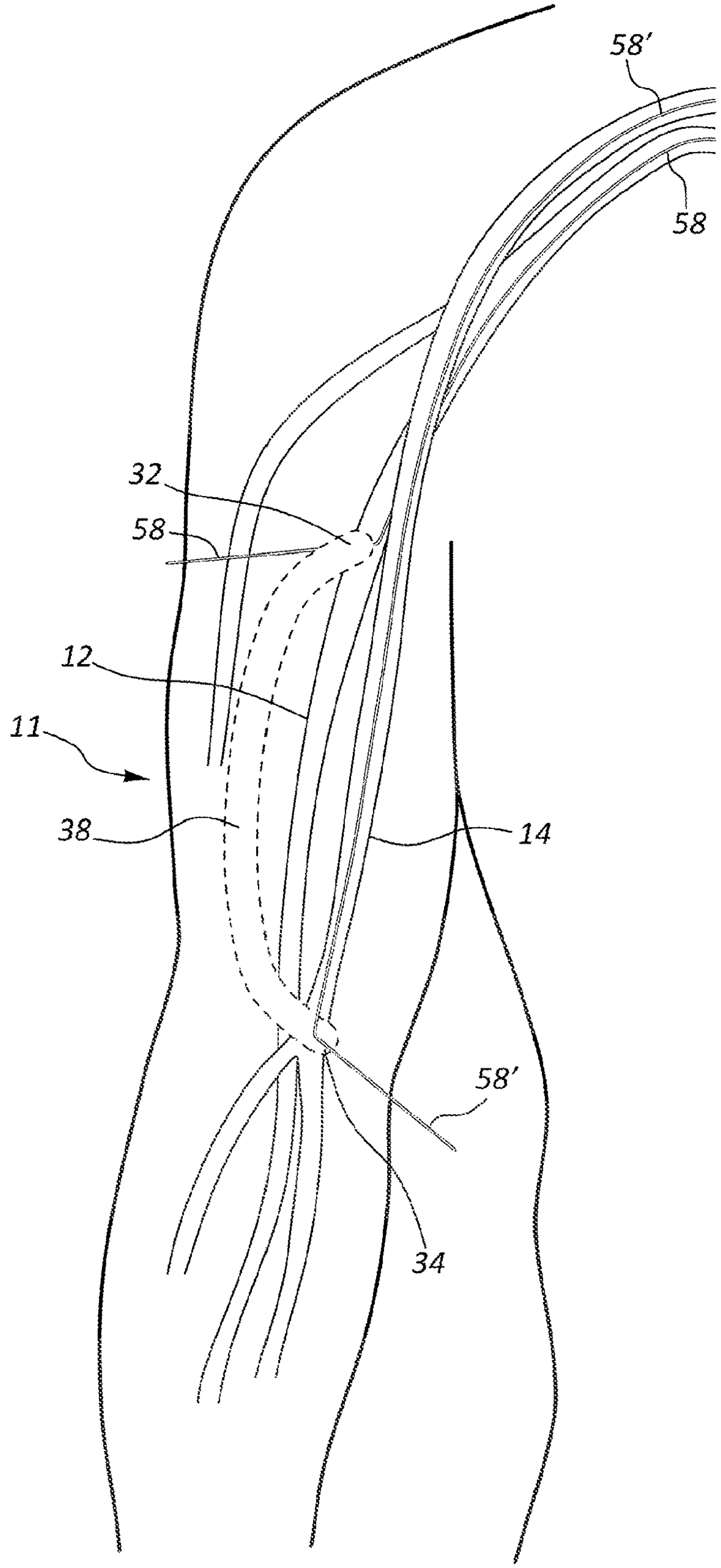
FIG. 11B is a schematic cross-sectional view of the arterial and venous vasculature of the patient's right arm illustrating a subcutaneous tunnel between the arterial exit site and the venous exit site.

FIGS. 11A and 11B depict the stylets 58, 58' as illustrated in FIGS. 10A and FIGS. 11A and 11B show a subcutaneous tunnel 38 formed in the right upper arm 11. The tunnel 38 extends from the venous exit site 32 in the axillary vein 12 to the arterial exit site 34 in the brachial artery 14. The tunnel 38 is configured such that a middle portion of the tunnel 38 is more superficial than end portions of the tunnel 38 to facilitate access of the AV graft during hemodialysis treatments as will be described below. The tunnel 38 can be formed by making a small incision adjacent the venous exit site 32. A straight or curved subcutaneous tunneling device (not shown) is inserted through the incision into the subcutaneous tissue and directed toward the arterial exit site 34. The tunneling device is forced through the subcutaneous tissue until a tunnel 38 is formed from the venous exit site 32 to the arterial exit site 34. The tunneling device is removed from the subcutaneous tissue. In some embodiments, the incision is made at the arterial exit site 34 and the tunneling device is directed toward the venous exit site 32.

Figure 12A:
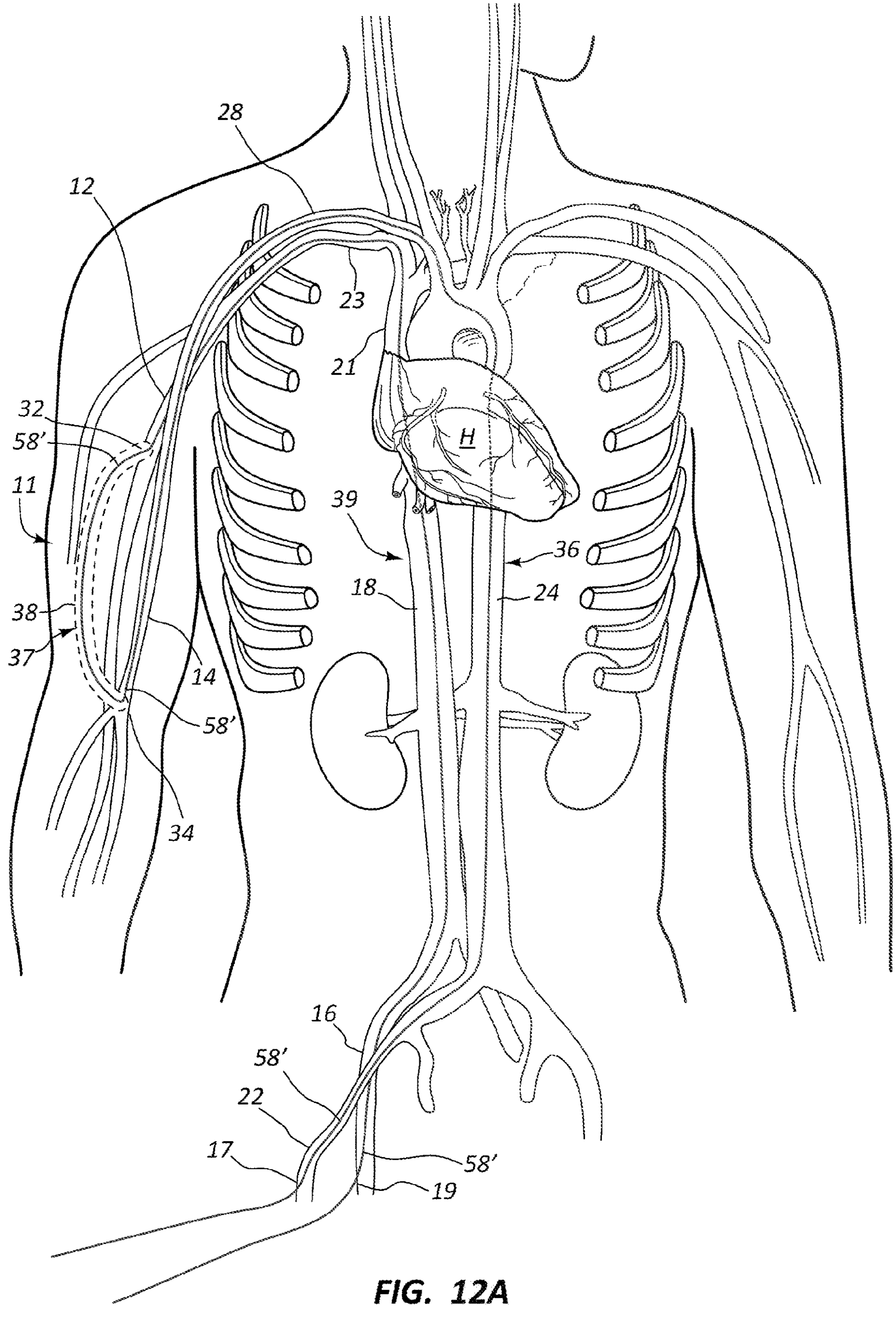
FIG. 12A is a schematic cross-sectional view of arterial and venous vasculatures of the patient illustrating the first stylet of the device of FIG. 1 forming a loop through a patient's arterial vasculature, through the subcutaneous tunnel, and through the patient's venous vasculature.
Figure 12B:
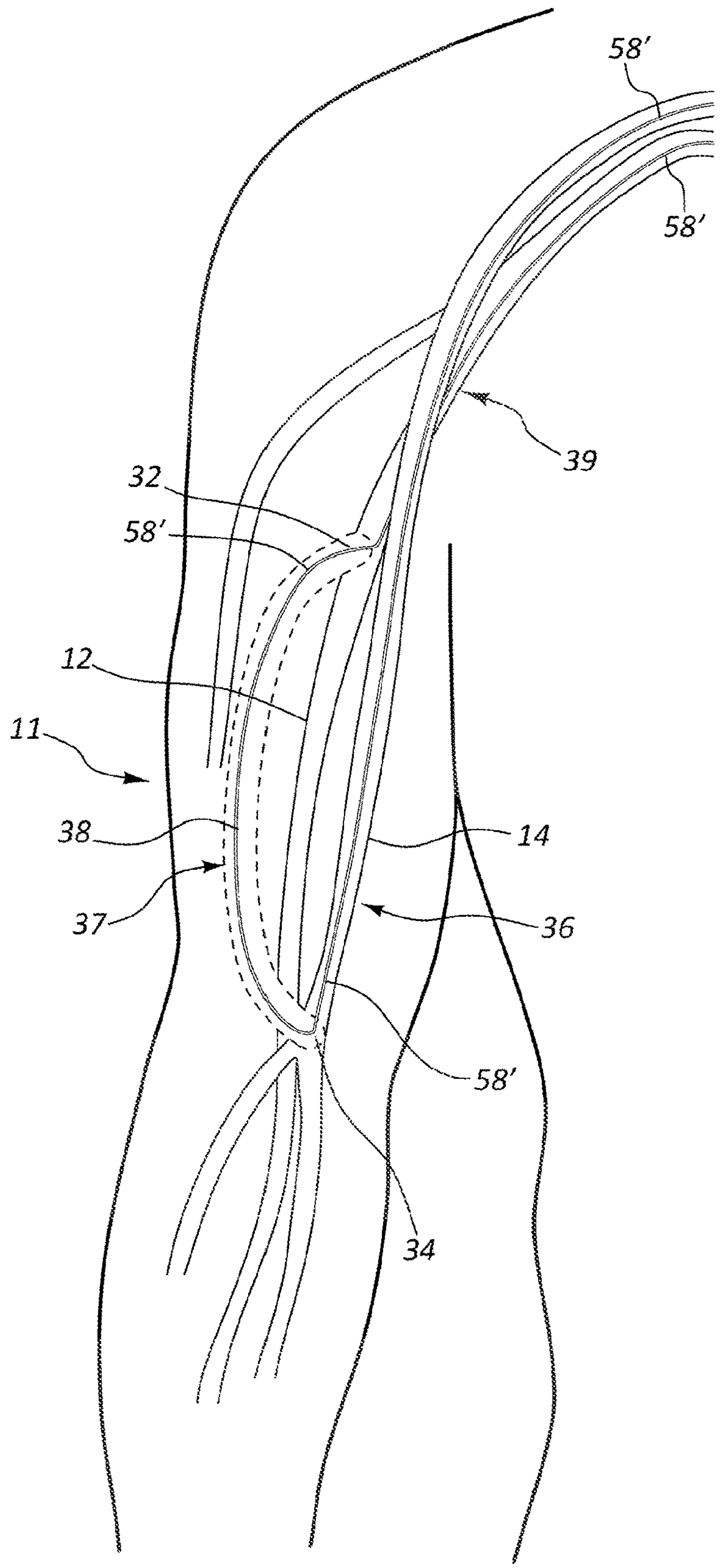
FIG. 12B is a schematic cross-sectional view of the arterial and venous vasculature of the patient's right arm illustrating the first stylet of the access device of FIG. 1 forming a loop through the brachial artery, through the subcutaneous tunnel, and through the axillary vein.

FIGS. 12A and 12B show a configuration of the stylet 58' following passage of a guide catheter (not shown) over the stylet 58 and through the tunnel 38 such that a distal end of the guide catheter is disposed adjacent the arterial exit site 34. The stylet 58' is partially retracted such that the distal end of the stylet 58' can be directed into a lumen of the guide catheter. The stylet 58 is retracted and removed from the guide catheter. The stylet 58' is advanced through the guide catheter until the distal end of the stylet 58' exits a proximal end of the guide catheter. The guide catheter is removed from the stylet 58'. As shown in FIGS. 12A and 12B, the stylet 58' is depicted to enter the femoral artery 22 at the arterial access site 17, pass through the arterial vasculature to the brachial artery 14, and exit the brachial artery 14 at the arterial exit site 34. The stylet 58' continues to pass through the tunnel 38, enter the axillary vein 12 at the venous exit site 32, pass through the venous vasculature into the femoral vein 16, and exit the femoral vein 16 at the venous access site 19. As shown in FIGS. 12A and 12B, the stylet 58' is configured to form a loop comprising an arterial leg 36 through the arterial vasculature, a tunnel leg 37 through the tunnel 38, and a venous leg 39 through the venous vasculature.

Figure 13A:
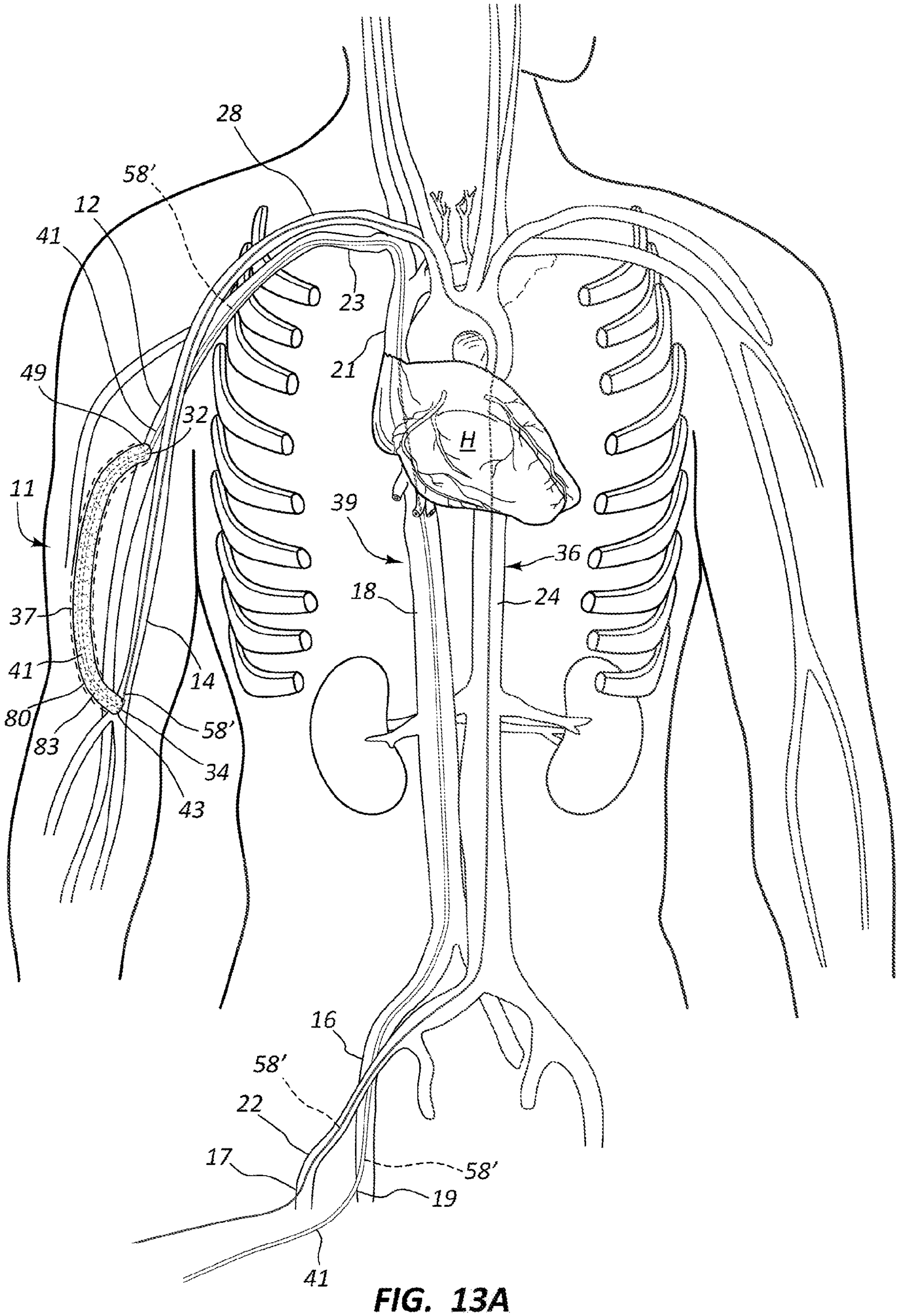
FIG. 13A is a schematic cross-sectional view of arterial and venous vasculatures of the patient illustrating the arterio-venous graft of FIG. 6A implanted in the arm.
Figure 13B:
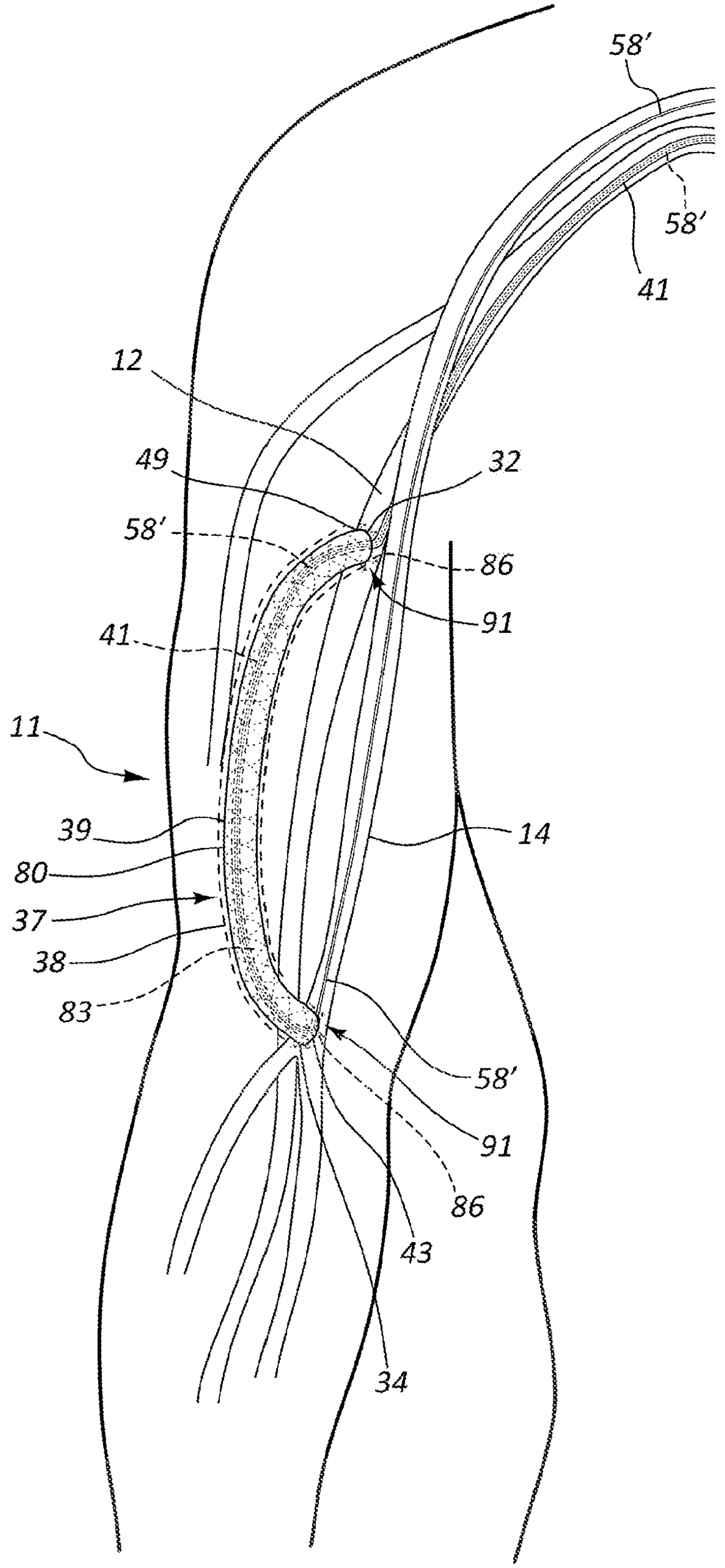
FIG. 13B is a schematic cross-sectional view of the arterial and venous vasculature of the patient's right arm illustrating the arterio-venous graft of FIG. 6A implanted in the arm.

FIGS. 13A and 13B depict implantation of the AV graft 80. The stylet 58' is shown as depicted in FIGS. 12A and 12B. A graft delivery catheter 41, configured with the AV graft 80 at a distal end portion, is threaded over an end of the stylet 58' extending from the femoral vein 16 and over the venous leg 39 and tunnel leg 37 of the stylet 58'. A distal end of the delivery catheter 41 and a distal end of the AV graft 80 are advanced through the arterial exit site 34 into the brachial artery 14. A proximal end of the AV graft 80 is disposed through the venous exit site 32 and within the axillary vein 12. The AV graft 80 is released from the delivery catheter 41 and radially expanded within the tunnel 38. The distal end of the AV graft 80 is displaced proximally such that the hooks 86 of the anchors 91 penetrate the wall of the brachial artery 14 to form an arterial sutureless anastomosis 43. The proximal end of the AV graft 80 is displaced distally such that the hooks 86 of the anchors 91 penetrate the wall of the axillary vein 12 to form a venous sutureless anastomosis 49. The stylet 58' and the delivery catheter 41 are retracted and removed from the patient. The bore 83 of the AV graft 80 is fluidly coupled to the brachial artery 14 and the axillary vein 12 such that blood flows from the brachial artery 14 through the AV graft 80 and into the axillary vein 12. Implantation of other types of grafts, such as balloon expandable grafts, non-stent grafts, tissue engineered grafts, bovine grafts, allografts, etc., is contemplated within the scope of this application.

Subsequent to implantation of the AV graft 80, the AV graft 80 can be used to treat the renal failure patient with hemodialysis. The AV graft 80 can be palpated through the skin of the patient by a healthcare worker and accessed with hemodialysis needles. The needles can be fluidly coupled to a hemodialysis set including a filter. The set can be coupled to a dialysis machine. Blood can be withdrawn from the AV graft 80 through an arterial dialysis needle, passed through the filter to remove toxins, and returned to the AV graft 80 and the patient. Hemodialysis treatments may be delivered three to five times a week.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A method of percutaneously implanting an arterio-venous graft, comprising:

advancing a first guidewire into a lumen of a first artery from a second artery; advancing a second guidewire into a lumen of a first vein from a second vein;

advancing a first access catheter over the first guidewire into the lumen of the first artery;

advancing a second access catheter over the second guidewire into the lumen of the first vein;

operating a first guide tube actuator to advance a first guide tube from the first access catheter toward a portion of a wall of the first artery;

operating a second guide tube actuator to advance a second guide tube from the second access catheter toward a portion of a wall of the first vein;

operating a first stylet actuator to advance a first stylet along a curved path through the first guide tube and through the wall of the first artery to form an arterial exit site;

operating a second stylet actuator to advance a second stylet along a curved path through the second guide tube and through the wall of the first vein to form a venous exit site; and forming a subcutaneous tunnel between the arterial exit site and the venous exit site, wherein the subcutaneous tunnel is located in an arm of a patient.

2. The method of claim 1, further comprising: advancing a guide catheter over the second stylet; wherein the guide catheter passes through the venous exit site and through the subcutaneous tunnel; and wherein a distal end of the guide catheter is disposed adjacent the arterial exit site.

3. The method of claim 2, further comprising:

threading the first stylet through the guide catheter, wherein the first stylet forms a loop comprising an arterial leg, a venous leg, and a tunnel leg.

4. The method of claim 3, further comprising: threading a delivery catheter comprising the arterio-venous graft over the venous leg and the tunnel leg of the loop of the first stylet; and deploying the arterio-venous graft such that a distal end of the arterio-venous graft is coupled to the first artery, a body is disposed within the subcutaneous tunnel, and a proximal end of the arterio-venous graft is coupled to the first vein.

5. The method of claim 4, wherein the arterio-venous graft comprises a plurality of anchors disposed about a periphery of the distal end and the proximal end.

6. The method of claim 5, wherein the plurality of anchors comprise at least one hook member.

7. The method of claim 6, further comprising:

forming a sutureless anastomosis at the arterial exit site between the distal end of the arterio-venous graft and the first artery, wherein the hook member is embedded into the wall of the first artery adjacent the arterial exit site; and forming a sutureless anastomosis at the venous exit site between the proximal end of the arterio-venous graft and the first vein, wherein the hook member is embedded into the wall of the first vein adjacent the venous exit site.

8. The method of claim 7, wherein blood flows from the first artery, through the arterio-venous graft and into the first vein.

9. The method of claim 5, wherein each anchor of the plurality of anchors includes a pair of struts that are partially disposed outside the arterio-venous graft and extend radially outward substantially perpendicular to the arterio-venous graft and form an apex disposed outside the arterio-venous graft.

10. The method of claim 9, wherein a hook member extends from each apex.

11. The method of claim 10, wherein each hook member forms an acute angle relative to the pair of struts.

12. The method of claim 9, wherein the pair of struts of each anchor forms a 90 degree angle between the struts.

13. The method of claim 4, wherein the arterio-venous graft is configured as a self-expanding, covered stent graft.

14. The method claim 1, wherein the first artery is a brachial artery and the second artery is a femoral artery.

15. The method of claim 1, wherein the first vein is an axillary vein and the second vein is a femoral vein.

16. The method of claim 1, wherein the first stylet advances through subcutaneous tissue and skin adjacent to the first artery.

17. The method of claim 1, wherein the second stylet advances through subcutaneous tissue and skin adjacent to the first vein.

18. The method of claim 1, wherein a middle portion of the subcutaneous tunnel is more superficial than end portions of the subcutaneous tunnel disposed at the arterial exit site and the venous exit site, respectively.

* * * * *